(12) United States Patent
Whitfill

(10) Patent No.: US 11,850,267 B2
(45) Date of Patent: *Dec. 26, 2023

(54) METHODS AND COMPOSITIONS FOR TREATING SKIN DISEASE WITH RECOMBINANT MICROORGANISMS

(71) Applicant: Azitra Inc, Farmington, CT (US)

(72) Inventor: Travis Michael Whitfill, Dallas, TX (US)

(73) Assignee: Azitra Inc, Branford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 17/062,832

(22) Filed: Oct. 5, 2020

(65) Prior Publication Data

US 2021/0121504 A1 Apr. 29, 2021

Related U.S. Application Data

(63) Continuation of application No. PCT/US2019/026045, filed on Apr. 5, 2019.

(60) Provisional application No. 62/653,021, filed on Apr. 5, 2018.

(51) Int. Cl.
*A61K 35/74* (2015.01)
*C07K 14/31* (2006.01)

(52) U.S. Cl.
CPC .............. *A61K 35/74* (2013.01); *C07K 14/31* (2013.01); *C07K 2319/00* (2013.01)

(58) Field of Classification Search
None
See application file for complete search history.

(56) References Cited

U.S. PATENT DOCUMENTS

| 2013/0018000 A1 | 1/2013 | Stout |
| 2015/0315574 A1 | 11/2015 | Wilusz et al. |
| 2018/0021412 A1 | 1/2018 | Angel et al. |
| 2018/0086807 A1 | 3/2018 | Bancel et al. |

FOREIGN PATENT DOCUMENTS

| AU | 2014203006 A1 | 6/2014 |
| WO | 2007/068946 A3 | 12/2007 |
| WO | 2015/184134 A1 | 12/2015 |
| WO | 2019/050898 A1 | 3/2019 |

OTHER PUBLICATIONS

Stout et al., Recombinant filaggrin is internalized and processed to correct filaggrin deficiency. J Invest Dermatol. Feb. 2014;134(2):423-429.

International Search Report and Written Opinion for Application No. PCT/US2019/026045, dated Jul. 10, 2019, 13 pages.

*Primary Examiner* — Brian Gangle
(74) *Attorney, Agent, or Firm* — McCarter & English, LLP; Jonathan M. Sparks

(57) ABSTRACT

The present invention provides isolated plasmids, recombinant microorganisms, kits, and methods for the treatment of inflammatory skin disease.

10 Claims, 22 Drawing Sheets

Specification includes a Sequence Listing.

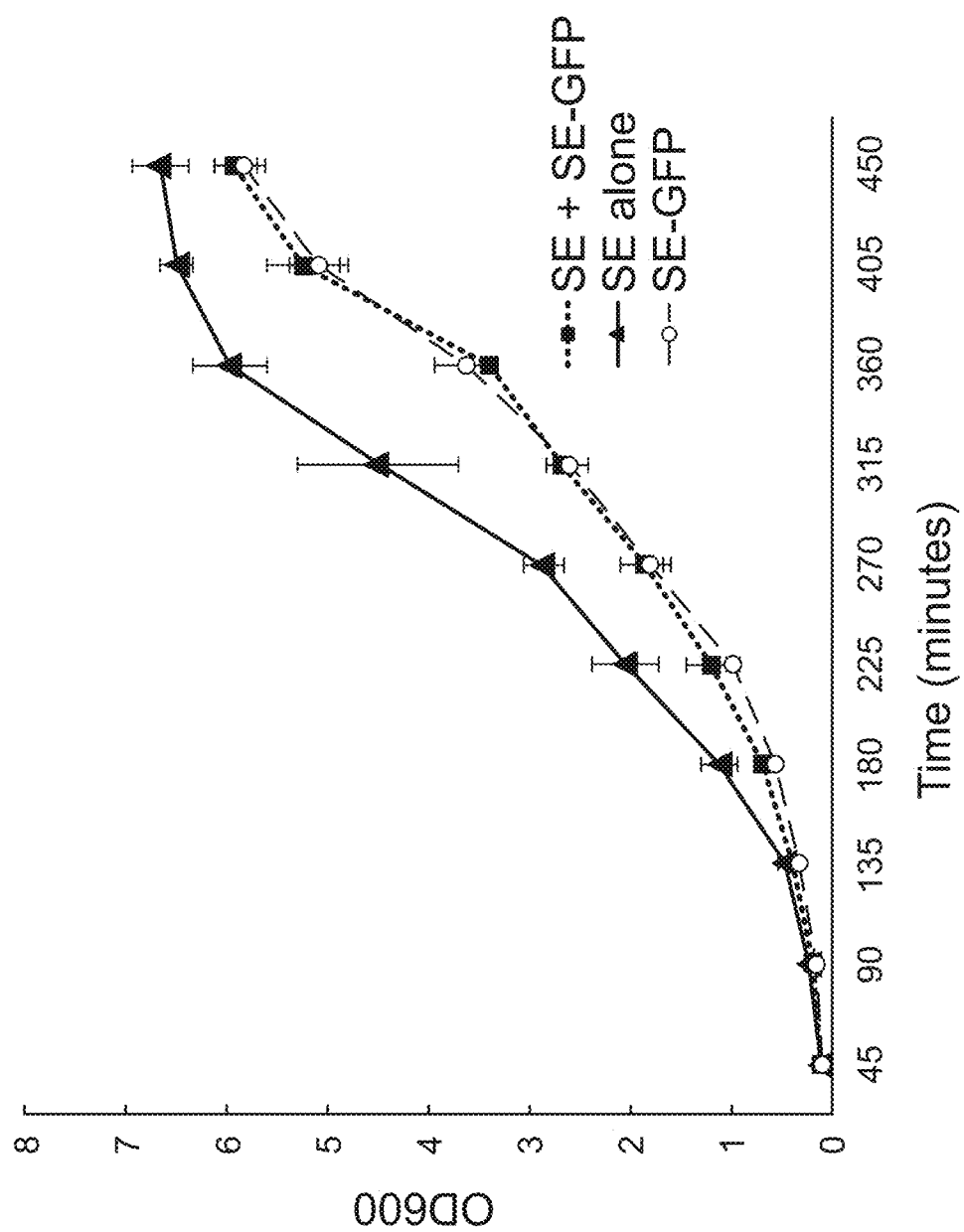

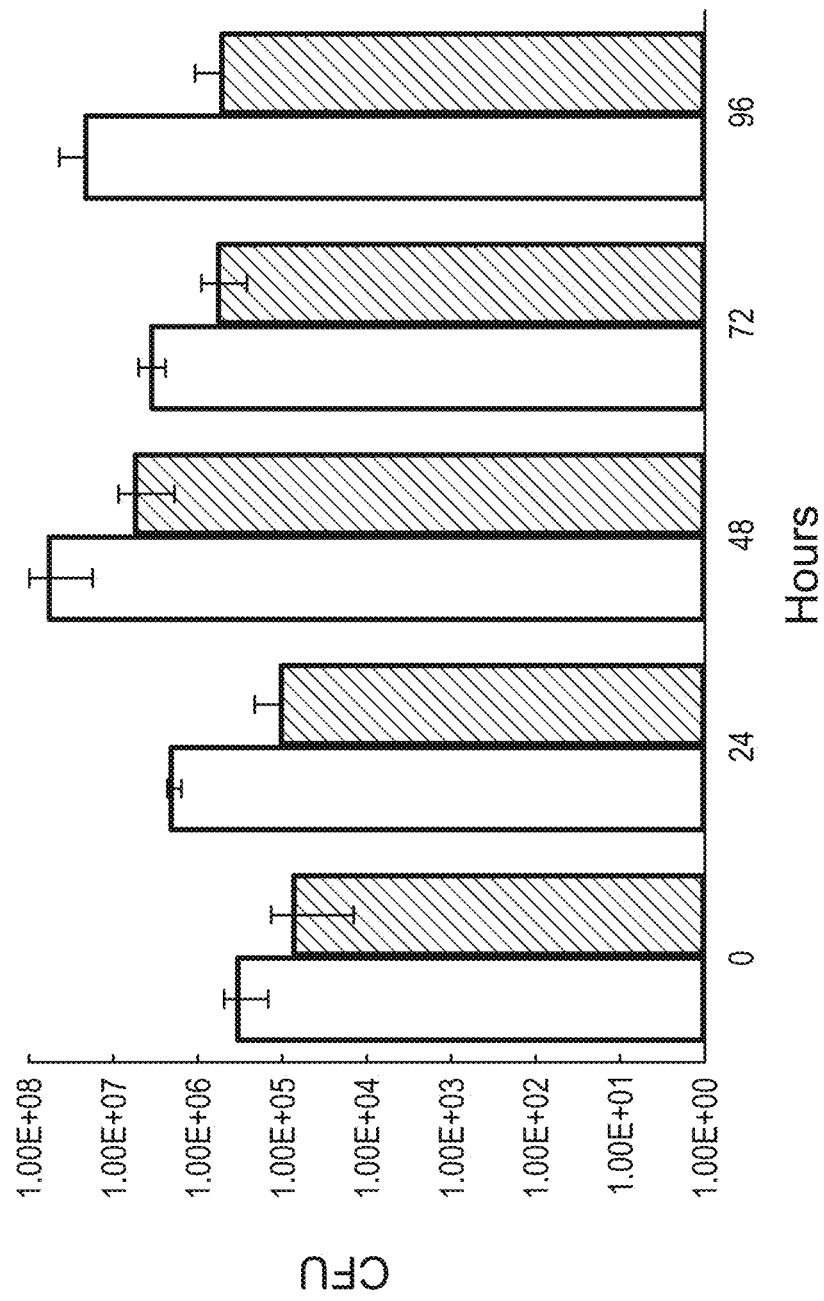

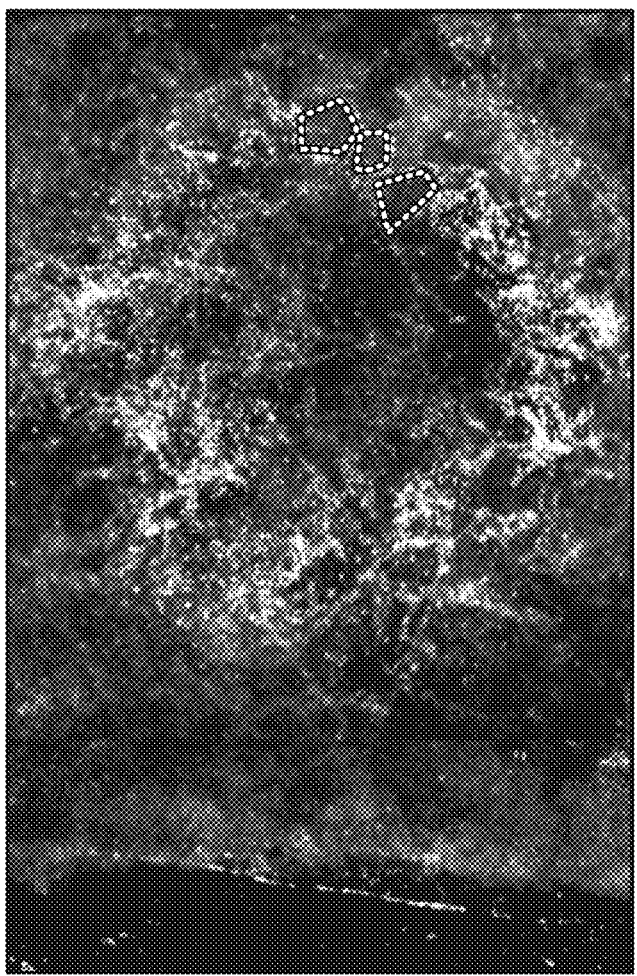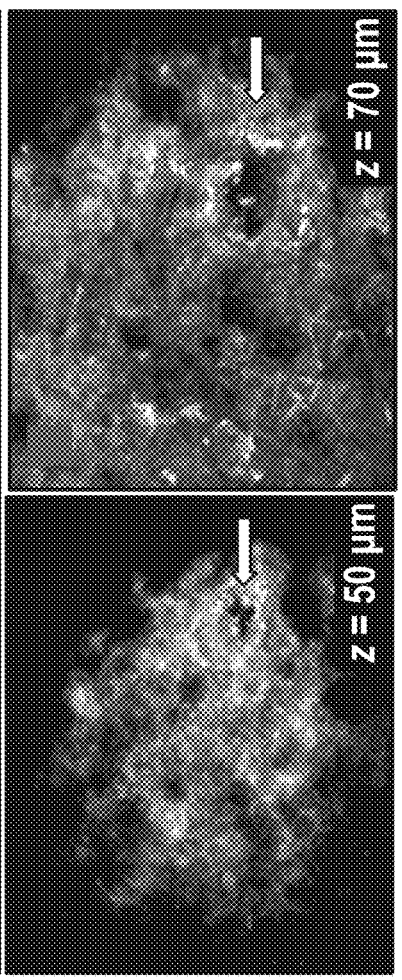

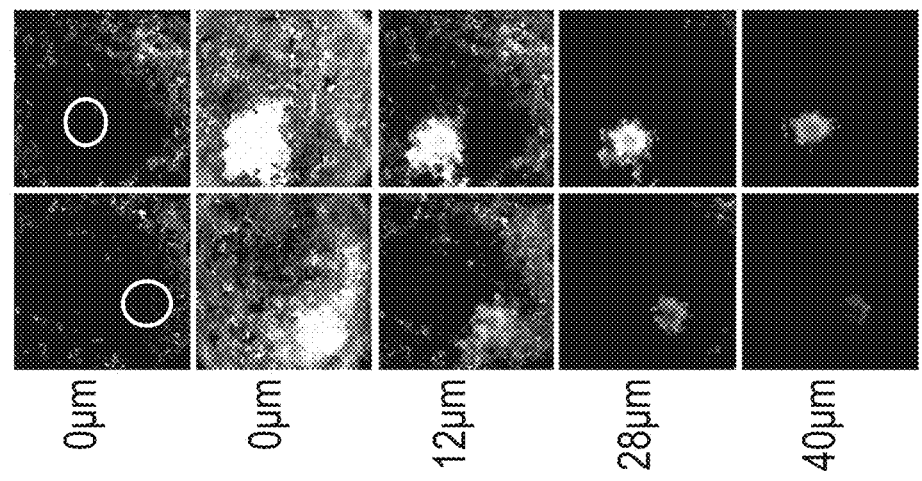
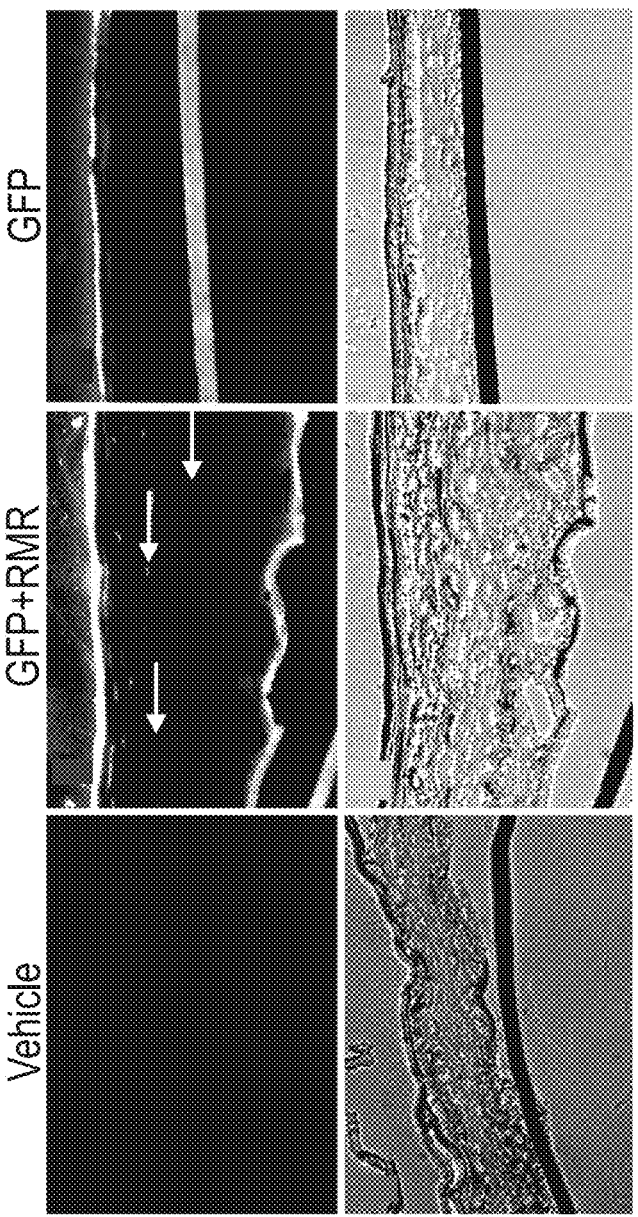

```
      1430       1440
        MQ   SGESSGRSRS
1450       1460       1470       1480       1490       1500
FLYQVSSHEQ SESTHGQTAP STGGRQGSRH EQARNSSRHS ASQDGQDTIR GHPGSSRGGR
1510       1520       1530       1540       1550       1560
QGSYHEQSVD RSGHSGYHHS HTTPQGRSDA SHGQSGPRSA SRQTRNEEQS GDGSRHSGSR
1570       1580       1590       1600       1610       1620
HHEPSTRAGS SRHSQVGQGE SAGSKTSRRQ GSSVSQDRDS EGHSEDSERR SESASRNHYG
1630       1640       1650       1660       1670       1680
SAREQSRHGS RNPRSHQEDR ASHGHSAESS RQSGTRHAET SSGGQAASSQ EGARSSPGER
1690       1700       1710       1720       1730       1740
HGSRHQQSAD SSTDSGTGRR QDSSVVGDSG NRGSSSGSQAS DSEGHSEESD TQSVSAHGQA
1750       1760       1770
GPHQQSHQES TRGQSGERSG RSGSFLYQVS THEQSESRMR RMRRMRR
```

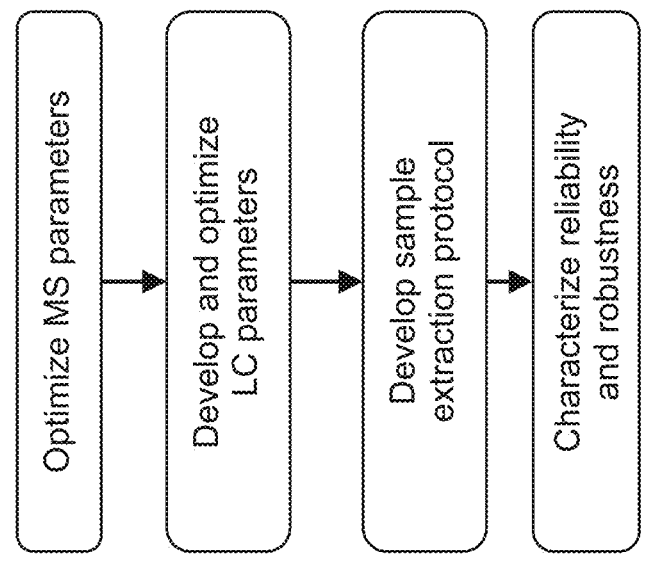
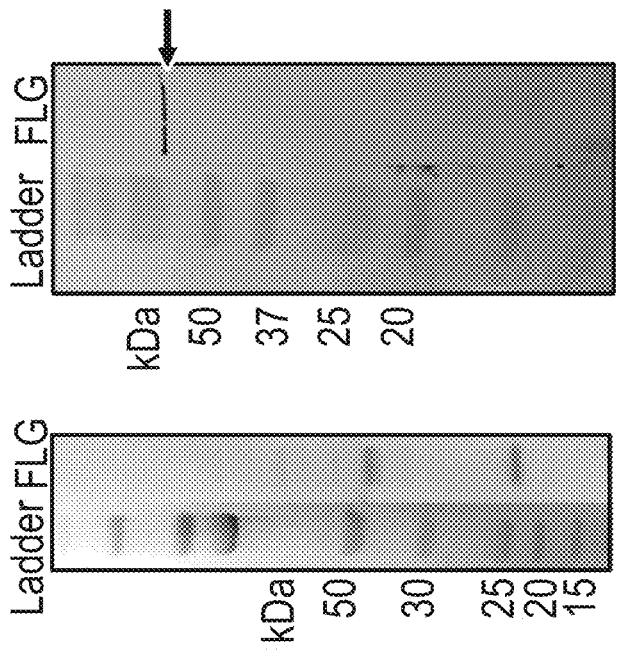
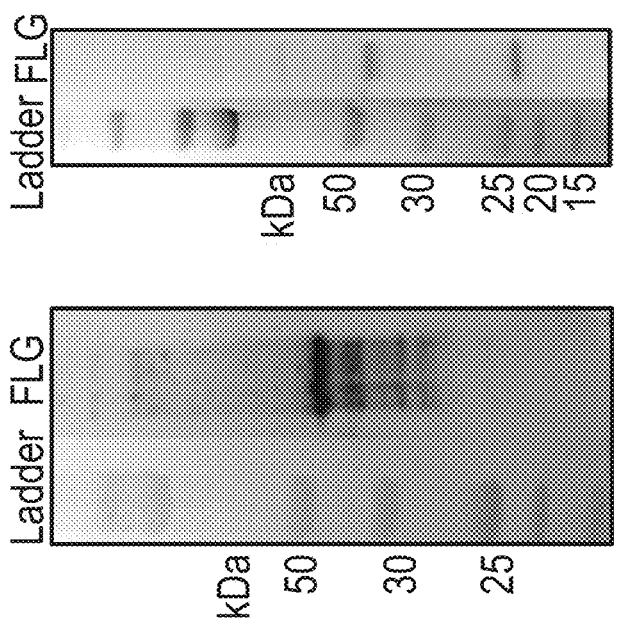
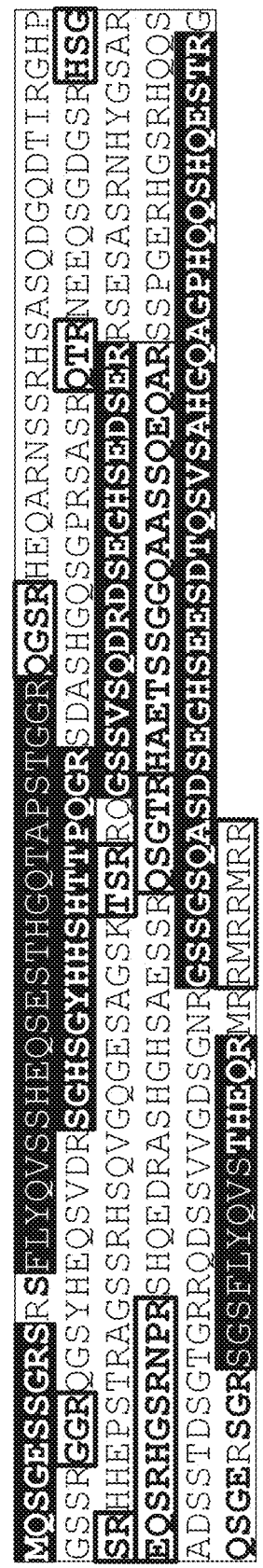
FIG. 7A  FIG. 7B  FIG. 7C  FIG. 7D  FIG. 7E

```
                        SEQUENCE LISTING

<160> NUMBER OF SEQ ID NOS: 29

<210> SEQ ID NO 1
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gln Ser Gly Glu Ser Ser Gly Arg Ser Arg Ser Phe Leu Tyr Gln
1               5                   10                  15

Val Ser Ser His Glu Gln Ser Glu Ser Thr His Gly Gln Thr Ala Pro
            20                  25                  30

Ser Thr Gly Gly Arg Gln Gly Ser Arg His Glu Gln Ala Arg Asn Ser
        35                  40                  45

Ser Arg His Ser Ala Ser Gln Asp Gly Gln Asp Thr Ile Arg Gly His
    50                  55                  60

Pro Gly Ser Ser Arg Gly Gly Arg Gln Gly Ser Tyr His Glu Gln Ser
65                  70                  75                  80
```

Val Asp Arg Ser Gly His Ser Gly Tyr His His Ser His Thr Thr Pro
            85                  90                  95

Gln Gly Arg Ser Asp Ala Ser His Gly Gln Ser Gly Pro Arg Ser Ala
        100                 105                 110

Ser Arg Gln Thr Arg Asn Glu Glu Gln Ser Gly Asp Gly Ser Arg His
    115                 120                 125

Ser Gly Ser Arg His His Glu Pro Ser Thr Arg Ala Gly Ser Ser Arg
130                 135                 140

His Ser Gln Val Gly Gln Gly Glu Ser Ala Gly Ser Lys Thr Ser Arg
145                 150                 155                 160

Arg Gln Gly Ser Ser Val Ser Gln Asp Arg Asp Ser Glu Gly His Ser
                165                 170                 175

Glu Asp Ser Glu Arg Arg Ser Glu Ser Ala Ser Arg Asn His Tyr Gly
            180                 185                 190

Ser Ala Arg Glu Gln Ser Arg His Gly Ser Arg Asn Pro Arg Ser His
        195                 200                 205

Gln Glu Asp Arg Ala Ser His Gly His Ser Ala Glu Ser Ser Arg Gln
    210                 215                 220

Ser Gly Thr Arg His Ala Glu Thr Ser Ser Gly Gly Gln Ala Ala Ser
225                 230                 235                 240

Ser Gln Glu Gln Ala Arg Ser Ser Pro Gly Glu Arg His Gly Ser Arg
                245                 250                 255

His Gln Gln Ser Ala Asp Ser Ser Thr Asp Ser Gly Thr Gly Arg Arg
            260                 265                 270

Gln Asp Ser Ser Val Val Gly Asp Ser Gly Asn Arg Gly Ser Ser Gly
        275                 280                 285

Ser Gln Ala Ser Asp Ser Glu Gly His Ser Glu Ser Asp Thr Gln
    290                 295                 300

Ser Val Ser Ala His Gly Gln Ala Gly Pro His Gln Ser His Gln
305                 310                 315                 320

Glu Ser Thr Arg Gly Gln Ser Gly Glu Arg Ser Gly Arg Ser Gly Ser
                325                 330                 335

Phe Leu Tyr Gln Val Ser Thr His Glu Gln Ser Glu Ser Arg Met Arg
            340                 345                 350

Arg Met Arg Arg Met Arg Arg
        355

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Met Arg Arg Met Arg Met Arg Arg
1               5                   10

<210> SEQ ID NO 3
<211> LENGTH: 23
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Any amino acid
<220> FEATURE:

```
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (17)..(17)
<223> OTHER INFORMATION: Any amino acid

<400> SEQUENCE: 3

Gln Ser Gly Glu Xaa Ser Gly Arg Xaa Ser Phe Leu Tyr Gln Val Ser
1               5                   10                  15

Xaa His Glu Gln Ser Glu Ser
            20

<210> SEQ ID NO 4
<211> LENGTH: 171
<212> TYPE: PRT
<213> ORGANISM: Homo sapiens

<400> SEQUENCE: 4

Glu Arg Ser Arg Ser Ser Asp Gly Lys Ser Ser Gln Val Asn Arg
1               5                   10                  15

Ser Arg His Glu Asn Thr Ser Gln Val Pro Leu Gln Glu Ser Arg Thr
            20                  25                  30

Arg Lys Arg Arg Gly Ser Arg Val Ser Gln Asp Arg Asp Ser Glu Gly
        35                  40                  45

His Ser Glu Asp Ser Glu Arg His Ser Gly Ser Ala Ser Arg Asn His
    50                  55                  60

His Gly Ser Ala Trp Glu Gln Ser Arg Asp Gly Ser Arg His Pro Arg
65                  70                  75                  80

Ser His Asp Glu Asp Arg Ala Ser His Gly His Ser Ala Asp Ser Ser
                85                  90                  95

Arg Gln Ser Gly Thr Arg His Ala Glu Thr Ser Ser Arg Gly Gln Thr
            100                 105                 110

Ala Ser Ser His Glu Gln Ala Arg Ser Ser Pro Gly Glu Arg His Gly
        115                 120                 125

Ser Gly His Gln Gln Ser Ala Asp Ser Ser Arg His Ser Ala Thr Gly
    130                 135                 140

Arg Gly Gln Ala Ser Ser Ala Val Ser Asp Arg Gly His Arg Gly Ser
145                 150                 155                 160

Ser Gly Ser Gln Ala Ser Asp Ser Glu Gly His
                165                 170

<210> SEQ ID NO 5
<211> LENGTH: 174
<212> TYPE: PRT
<213> ORGANISM: Homo sapiens

<400> SEQUENCE: 5

Asp Gly Ser Arg His Ser Gly Ser His His Glu Ala Ser Ser Trp
1               5                   10                  15

Ala Asp Ser Ser Arg His Ser Leu Val Gly Gln Gly Gln Ser Ser Gly
            20                  25                  30

Pro Arg Thr Ser Arg Pro Arg Gly Ser Ser Val Ser Gln Asp Ser Asp
        35                  40                  45

Ser Glu Gly His Ser Glu Asp Ser Glu Arg Ser Gly Ser Ala Ser
    50                  55                  60

Arg Asn His His Gly Ser Ala Gln Glu Gln Ser Arg Asp Gly Ser Arg
65                  70                  75                  80
```

His Pro Arg Ser His His Glu Asp Arg Ala Gly His Gly His Ser Ala
                85                  90                  95

Glu Ser Ser Arg Gln Ser Gly Thr His His Ala Glu Asn Ser Ser Gly
            100                 105                 110

Gly Gln Ala Ala Ser Ser His Glu Gln Ala Arg Ser Ser Ala Gly Glu
        115                 120                 125

Arg His Gly Ser His His Gln Gln Ser Ala Asp Ser Ser Arg His Ser
    130                 135                 140

Gly Ile Gly His Gly Gln Ala Ser Ser Ala Val Arg Asp Ser Gly His
145                 150                 155                 160

Arg Gly Ser Ser Gly Ser Gln Ala Ser Asp Ser Glu Gly His
                165                 170

<210> SEQ ID NO 6
<211> LENGTH: 174
<212> TYPE: PRT
<213> ORGANISM: Homo sapiens

<400> SEQUENCE: 6

Asp Gly Ser Arg His Ser Trp Ser His His His Glu Ala Ser Thr Gln
1               5                   10                  15

Ala Asp Ser Ser Arg His Ser Gln Ser Gly Gln Gly Gln Ser Ala Gly
            20                  25                  30

Pro Arg Thr Ser Arg Asn Gln Gly Ser Ser Val Ser Gln Asp Ser Asp
        35                  40                  45

Ser Gln Gly His Ser Glu Asp Ser Glu Arg Trp Ser Gly Ser Ala Ser
    50                  55                  60

Arg Asn His Arg Gly Ser Ala Gln Glu Gln Ser Arg Asp Gly Ser Arg
65                  70                  75                  80

His Pro Thr Ser His His Glu Asp Arg Ala Gly His Gly His Ser Ala
                85                  90                  95

Glu Ser Ser Arg Gln Ser Gly Thr His His Ala Glu Asn Ser Ser Gly
            100                 105                 110

Gly Gln Ala Ala Ser Ser His Glu Gln Ala Arg Ser Ser Ala Gly Glu
        115                 120                 125

Arg His Gly Ser His His Gln Gln Ser Ala Asp Ser Ser Arg His Ser
    130                 135                 140

Gly Ile Gly His Gly Gln Ala Ser Ser Ala Val Arg Asp Ser Gly His
145                 150                 155                 160

Arg Gly Ser Ser Gly Ser Gln Ala Ser Asp Ser Glu Gly His
                165                 170

<210> SEQ ID NO 7
<211> LENGTH: 174
<212> TYPE: PRT
<213> ORGANISM: Homo sapiens

<400> SEQUENCE: 7

Asp Gly Ser Arg His Ser Gly Ser Arg His His Glu Pro Ser Thr Arg
1               5                   10                  15

Ala Gly Ser Ser Arg His Ser Gln Val Gly Gln Gly Glu Ser Ala Gly
            20                  25                  30

Ser Lys Thr Ser Arg Arg Gln Gly Ser Ser Val Ser Gln Asp Arg Asp
        35                  40                  45

Ser Glu Gly His Ser Glu Asp Ser Glu Arg Arg Ser Glu Ser Ala Ser
    50                  55                  60

Arg Asn His Tyr Gly Ser Ala Arg Glu Gln Ser Arg His Gly Ser Arg
65                  70                  75                  80

Asn Pro Arg Ser His Gln Glu Asp Arg Ala Ser His Gly His Ser Ala
                85                  90                  95

Glu Ser Ser Arg Gln Ser Gly Thr Arg His Ala Glu Thr Ser Ser Gly
            100                 105                 110

Gly Gln Ala Ala Ser Ser Gln Glu Gln Ala Arg Ser Ser Pro His Glu
        115                 120                 125

Arg His Gly Ser Arg His Gln Gln Ser Ala Asp Ser Ser Thr Asp Ser
    130                 135                 140

Gly Thr Gly Arg Arg Gln Asp Ser Ser Val Val Gly Asp Ser Gly Asn
145                 150                 155                 160

Arg Gly Ser Ser Gly Ser Gln Ala Ser Asp Ser Glu Gly His
                165                 170

<210> SEQ ID NO 8
<211> LENGTH: 174
<212> TYPE: PRT
<213> ORGANISM: Homo sapiens

<400> SEQUENCE: 8

Asp Gly Ser Arg His Ser Gly Ser Arg His His Glu Ala Ala Ser Trp
1               5                   10                  15

Ala Asp Ser Ser Arg His Ser Gln Val Gly Gln Glu Gln Ser Ser Gly
            20                  25                  30

Ser Arg Thr Ser Arg His Gln Gly Ser Ser Val Ser Gln Asp Ser Asp
        35                  40                  45

Ser Glu Arg His Ser Asp Asp Ser Glu Arg Leu Ser Gly Ser Ala Ser
    50                  55                  60

Arg Asn His His Gly Ser Ser Arg Glu Gln Ser Arg Asp Gly Ser Arg
65                  70                  75                  80

His Pro Gly Phe His Gln Glu Asp Arg Ala Ser His Gly His Ser Ala
                85                  90                  95

Asp Ser Ser Arg Gln Ser Gly Thr His His Thr Glu Ser Ser Ser His
            100                 105                 110

Gly Gln Ala Val Ser Ser His Glu Gln Ala Arg Ser Ser Pro Gly Glu
        115                 120                 125

Arg His Gly Ser Arg His Gln Gln Ser Ala Asp Ser Ser Arg His Ser
    130                 135                 140

Gly Ile Gly His Arg Gln Ala Ser Ser Ala Val Arg Asp Ser Gly His
145                 150                 155                 160

Arg Gly Ser Ser Gly Ser Gln Val Thr Asn Ser Glu Gly His
                165                 170

<210> SEQ ID NO 9
<211> LENGTH: 174
<212> TYPE: PRT
<213> ORGANISM: Homo sapiens

<400> SEQUENCE: 9

Asp Gly Ser Arg His Ser Gly Ser Arg His His Glu Ala Ser Ser His
1               5                   10                  15

Ala Asp Ile Ser Arg His Ser Gln Ala Gly Gln Gly Gln Ser Glu Gly
            20                  25                  30

Ser Arg Thr Ser Arg Arg Gln Gly Ser Ser Val Ser Gln Asp Ser Asp
        35                  40                  45

```
Ser Glu Gly His Ser Glu Asp Ser Glu Arg Trp Ser Gly Ser Ala Ser
    50                  55                  60

Arg Asn His Arg Gly Ser Ala Gln Glu Gln Ser Arg His Gly Ser Arg
65                  70                  75                  80

His Pro Arg Ser His His Glu Asp Arg Ala Gly His Gly His Ser Ala
                85                  90                  95

Asp Ser Ser Arg Gln Ser Gly Thr Pro His Ala Glu Thr Ser Ser Gly
                100                 105                 110

Gly Gln Ala Ala Ser Ser His Glu Gln Ala Arg Ser Ser Pro Gly Glu
                115                 120                 125

Arg His Gly Ser Arg His Gln Gln Ser Ala Asp Ser Ser Arg His Ser
                130                 135                 140

Gly Ile Pro Arg Arg Gln Ala Ser Ser Ala Val Arg Asp Ser Gly His
145                 150                 155                 160

Trp Gly Ser Ser Gly Ser Gln Ala Ser Asp Ser Glu Gly His
                165                 170
```

```
<210> SEQ ID NO 10
<211> LENGTH: 174
<212> TYPE: PRT
<213> ORGANISM: Homo sapiens

<400> SEQUENCE: 10

Asp Gly Ser Arg His Ser Gly Ser Arg His His Glu Ala Ser Thr His
1               5                   10                  15

Ala Asp Ile Ser Arg His Ser Gln Ala Val Gln Gly Gln Ser Glu Gly
                20                  25                  30

Ser Arg Arg Ser Arg Arg Gln Gly Ser Ser Val Ser Gln Asp Ser Asp
            35                  40                  45

Ser Glu Gly His Ser Glu Asp Ser Glu Arg Trp Ser Gly Ser Ala Ser
    50                  55                  60

Arg Asn His His Gly Ser Ala Gln Glu Gln Leu Arg Asp Gly Ser Arg
65                  70                  75                  80

His Pro Arg Ser His Gln Glu Asp Arg Ala Gly His Gly His Ser Ala
                85                  90                  95

Asp Ser Ser Arg Gln Ser Gly Thr Arg His Thr Gln Thr Ser Ser Gly
                100                 105                 110

Gly Gln Ala Ala Ser Ser His Glu Gln Ala Arg Ser Ser Ala Gly Glu
                115                 120                 125

Arg His Gly Ser His His Gln Gln Ser Ala Asp Ser Ser Arg His Ser
                130                 135                 140

Gly Ile Gly His Gly Gln Ala Ser Ser Ala Val Arg Asp Ser Gly His
145                 150                 155                 160

Arg Gly Tyr Ser Gly Ser Gln Ala Ser Asp Asn Glu Gly His
                165                 170
```

```
<210> SEQ ID NO 11
<211> LENGTH: 174
<212> TYPE: PRT
<213> ORGANISM: Homo sapiens

<400> SEQUENCE: 11

Asp Ser Ser Arg His Ser Val Ser Arg His His Glu Ala Ser Thr His
1               5                   10                  15

Ala Asp Ile Ser Arg His Ser Gln Ala Val Gln Gly Gln Ser Glu Gly
                20                  25                  30
```

-continued

```
Ser Arg Arg Ser Arg Gln Gly Ser Ser Val Ser Gln Asp Ser Asp
            35                  40                  45

Ser Glu Gly His Ser Glu Asp Ser Glu Arg Trp Ser Gly Ser Ala Ser
 50                  55                  60

Arg Asn His Arg Gly Ser Val Gln Glu Gln Ser Arg His Gly His Arg
 65                  70                  75                  80

His Pro Arg Ser His His Glu Asp Arg Ala Gly His Gly His Ser Ala
                 85                  90                  95

Asp Arg Ser Arg Gln Ser Gly Thr Arg His Ala Glu Thr Ser Ser Gly
                100                 105                 110

Gly Gln Ala Ala Ser Ser His Gln Ala Arg Ser Ser Pro Gly Glu
                115                 120                 125

Arg His Gly Ser Arg His Gln Gln Ser Ala Asp Ser Ser Arg His Ser
130                 135                 140

Gly Ile Pro Arg Gly Gln Ala Ser Ser Ala Val Arg Asp Ser Arg His
145                 150                 155                 160

Trp Gly Ser Ser Gly Ser Gln Ala Ser Asp Ser Glu Gly His
                165                 170
```

<210> SEQ ID NO 12
<211> LENGTH: 174
<212> TYPE: PRT
<213> ORGANISM: Homo sapiens

<400> SEQUENCE: 12

```
Asp Gly Ser Arg His Ser Gly Ser Arg His His Glu Ala Ser Ser Arg
 1               5                  10                  15

Ala Asp Ser Ser Gly His Ser Gln Val Gly Gln Gly Gln Ser Glu Gly
                 20                  25                  30

Pro Arg Thr Ser Arg Asn Trp Gly Ser Ser Phe Ser Gln Asp Ser Asp
                 35                  40                  45

Ser Gln Gly His Ser Glu Asp Ser Glu Arg Trp Ser Gly Ser Ala Ser
 50                  55                  60

Arg Asn His His Gly Ser Ala Gln Glu Gln Leu Arg Asp Gly Ser Arg
 65                  70                  75                  80

His Pro Arg Ser His Gln Glu Asp Arg Ala Gly His Gly His Ser Ala
                 85                  90                  95

Asp Ser Ser Arg Gln Ser Gly Thr Arg His Thr Gln Thr Ser Ser Gly
                100                 105                 110

Gly Gln Ala Ala Ser Ser His Glu Gln Ala Arg Ser Ser Ala Gly Glu
                115                 120                 125

Arg His Gly Ser His His Gln Gln Ser Ala Asp Ser Ser Arg His Ser
130                 135                 140

Gly Ile Gly His Gly Gln Ala Ser Ser Ala Val Arg Asp Ser Gly His
145                 150                 155                 160

Arg Gly Tyr Ser Gly Ser Gln Ala Ser Asp Asn Glu Gly His
                165                 170
```

<210> SEQ ID NO 13
<211> LENGTH: 175
<212> TYPE: PRT
<213> ORGANISM: Homo sapiens

<400> SEQUENCE: 13

```
Asp Gly Thr Arg His Ser Gly Ser Arg His His Glu Ala Ser Ser Gln
 1               5                  10                  15
```

```
Ala Asp Ser Ser Arg His Ser Gln Val Gly Gln Gly Gln Ser Ser Gly
            20                  25                  30

Pro Arg Thr Ser Arg Asn Gln Gly Ser Ser Val Ser Gln Asp Ser Asp
        35                  40                  45

Ser Gln Gly His Ser Glu Asp Ser Glu Arg Trp Ser Gly Ser Ala Ser
 50                  55                  60

Arg Asn His His Gly Ser Ala Gln Glu Gln Ser Arg Asp Gly Ser Arg
 65                  70                  75                  80

His Pro Arg Ser His His Glu Asp Arg Ala Gly His Gly His Ser Ala
                85                  90                  95

Asp Ser Ser Arg Lys Ser Gly Thr Arg His Thr Gln Asn Ser Ser Ser
            100                 105                 110

Gly Gln Ala Ala Ser Ser His Glu Gln Ala Arg Ser Ser Ala Gly Glu
        115                 120                 125

Arg His Gly Ser Arg His Gln Leu Gln Ser Ala Asp Ser Ser Arg His
    130                 135                 140

Ser Gly Thr Gly His Gly Gln Ala Ser Ser Ala Val Arg Asp Ser Gly
145                 150                 155                 160

His Arg Gly Ser Ser Gly Ser Gln Ala Thr Asp Ser Glu Gly His
                165                 170                 175

<210> SEQ ID NO 14
<211> LENGTH: 175
<212> TYPE: PRT
<213> ORGANISM: Homo sapiens

<400> SEQUENCE: 14

Asp Gly Ser Arg His Ser Gly Ser Arg His His Glu Ala Ser Ser Arg
1               5                   10                  15

Ala Asp Ser Ser Arg His Ser Gln Val Gly Gln Gly Gln Ser Ser Gly
            20                  25                  30

Pro Arg Thr Ser Arg Asn Gln Gly Ser Ser Val Ser Gln Asp Ser Asp
        35                  40                  45

Ser Gln Gly His Ser Glu Asp Ser Glu Arg Trp Ser Gly Ser Ala Ser
 50                  55                  60

Arg Asn His Leu Gly Ser Ala Trp Glu Gln Ser Arg Asp Gly Ser Arg
 65                  70                  75                  80

His Pro Gly Ser His His Glu Asp Arg Ala Gly His Gly His Ser Ala
                85                  90                  95

Asp Ser Ser Arg Gln Ser Gly Thr Arg His Thr Glu Ser Ser Ser Arg
            100                 105                 110

Gly Gln Ala Ala Ser Ser His Glu Gln Ala Arg Ser Ser Ala Gly Glu
        115                 120                 125

Arg His Gly Ser His His Gln Leu Gln Ser Ala Asp Ser Ser Arg His
    130                 135                 140

Ser Gly Ile Gly His Gly Gln Ala Ser Ser Ala Val Arg Asp Ser Gly
145                 150                 155                 160

His Arg Gly Tyr Ser Gly Ser Gln Ala Ser Asp Ser Glu Gly His
                165                 170                 175

<210> SEQ ID NO 15
<211> LENGTH: 359
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 15

Met Gln Ser Gly Glu Ser Gly Arg Ser Arg Ser Phe Leu Tyr Gln
1               5                   10                  15

Val Ser Ser His Glu Gln Ser Gly Ser Thr His Gly Gln Thr Ala Pro
            20                  25                  30

Ser Thr Gly Gly Arg Gln Gly Ser Arg His Glu Gln Ala Arg Asn Ser
        35                  40                  45

Ser Arg His Ser Ala Ser Gln Asp Gly Gln Asp Thr Ile Arg Gly His
    50                  55                  60

Pro Gly Ser Ser Arg Gly Gly Arg Gln Gly Ser Tyr His Glu Gln Ser
65                  70                  75                  80

Val Asp Arg Ser Gly His Ser Gly Tyr His His Ser His Thr Thr Pro
                85                  90                  95

Gln Gly Arg Ser Asp Ala Ser His Gly Gln Ser Gly Pro Arg Ser Ala
            100                 105                 110

Ser Arg Gln Thr Arg Asn Glu Glu Gln Ser Gly Asp Gly Ser Arg His
        115                 120                 125

Ser Gly Ser Arg His His Glu Pro Ser Thr Arg Ala Gly Ser Ser Arg
    130                 135                 140

His Ser Gln Val Gly Gln Gly Glu Ser Ala Gly Ser Lys Thr Ser Arg
145                 150                 155                 160

Arg Gln Gly Ser Ser Val Ser Gln Asp Arg Asp Ser Glu Gly His Ser
                165                 170                 175

Glu Asp Ser Glu Arg Arg Ser Glu Ser Ala Ser Arg Asn His Tyr Gly
            180                 185                 190

Ser Ala Arg Glu Gln Ser Arg His Gly Ser Arg Asn Pro Arg Ser His
        195                 200                 205

Gln Glu Asp Arg Ala Ser His Gly His Ser Ala Glu Ser Ser Arg Gln
    210                 215                 220

Ser Gly Thr Arg His Ala Glu Thr Ser Ser Gly Gly Gln Ala Ala Ser
225                 230                 235                 240

Ser Gln Glu Gly Ala Arg Ser Ser Pro Gly Glu Arg His Gly Ser Arg
                245                 250                 255

His Gln Gln Ser Ala Asp Ser Ser Thr Asp Ser Gly Thr Gly Arg Arg
            260                 265                 270

Gln Asp Ser Ser Val Val Gly Asp Ser Gly Asn Arg Gly Ser Ser Gly
        275                 280                 285

Ser Gln Ala Ser Asp Ser Glu Gly His Ser Glu Glu Ser Asp Thr Gln
    290                 295                 300

Ser Val Ser Ala His Gly Gln Ala Gly Pro His Gln Ser His Gln
305                 310                 315                 320

Glu Ser Thr Arg Gly Gln Ser Gly Glu Arg Ser Gly Arg Ser Gly Ser
                325                 330                 335

Phe Leu Tyr Gln Val Ser Thr His Glu Gln Ser Glu Ser Arg Met Arg
            340                 345                 350

Arg Met Arg Arg Met Arg Arg
        355

<210> SEQ ID NO 16
<211> LENGTH: 356
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 16

Met Gln Ser Gly Glu Ser Gly Arg Ser Arg Ser Phe Leu Tyr Gln
1               5                   10                  15

Val Ser Ser His Glu Gln Ser Glu Ser Thr His Gly Gln Thr Ala Pro
            20                  25                  30

Ser Thr Gly Gly Arg Gln Gly Ser Arg His Glu Gln Ala Arg Asn Ser
        35                  40                  45

Ser Arg His Ser Ala Ser Gln Asp Gly Gln Asp Thr Ile Arg Gly His
    50                  55                  60

Pro Gly Ser Ser Arg Gly Gly Arg Gln Gly Ser Tyr His Glu Gln Ser
65                  70                  75                  80

Val Asp Arg Ser Gly His Ser Gly Tyr His His Ser His Thr Thr Pro
                85                  90                  95

Gln Gly Arg Ser Asp Ala Ser His Gly Gln Ser Gly Pro Arg Ser Ala
                100                 105                 110

Ser Arg Gln Thr Arg Asn Glu Glu Gln Ser Gly Asp Gly Ser Arg His
            115                 120                 125

Ser Gly Ser Arg His His Glu Pro Ser Thr Arg Ala Gly Ser Ser Arg
        130                 135                 140

His Ser Gln Val Gly Gln Gly Glu Ser Ala Gly Ser Lys Thr Ser Arg
145                 150                 155                 160

Arg Gln Gly Ser Ser Val Ser Gln Asp Arg Asp Ser Glu Gly His Ser
                165                 170                 175

Glu Asp Ser Glu Arg Arg Ser Glu Ser Ala Ser Arg Asn His Tyr Gly
                180                 185                 190

Ser Ala Arg Glu Gln Ser Arg His Gly Ser Arg Asn Pro Arg Ser His
            195                 200                 205

Gln Glu Asp Arg Ala Ser His Gly His Ser Ala Glu Ser Ser Arg Gln
210                 215                 220

Ser Gly Thr Arg His Ala Glu Thr Ser Ser Gly Gly Gln Ala Ala Ser
225                 230                 235                 240

Ser Gln Glu Gln Ala Arg Ser Ser Pro Gly Glu Arg His Gly Ser Arg
                245                 250                 255

His Gln Gln Ser Ala Asp Ser Ser Thr Asp Ser Gly Thr Gly Arg Arg
                260                 265                 270

Gln Asp Ser Ser Val Val Gly Asp Ser Gly Asn Arg Gly Ser Ser Gly
            275                 280                 285

Ser Gln Ala Ser Asp Ser Glu Gly His Ser Glu Glu Ser Asp Thr Gln
290                 295                 300

Ser Val Ser Ala His Gly Gln Ala Gly Pro His Gln Gln Ser His Gln
305                 310                 315                 320

Glu Ser Thr Arg Gly Gln Ser Gly Glu Arg Ser Gly Arg Ser Gly Ser
                325                 330                 335

Phe Leu Tyr Gln Val Ser Thr His Glu Gln Arg Met Arg Met Arg
            340                 345                 350

Arg Met Arg Arg
        355

<210> SEQ ID NO 17
<211> LENGTH: 23
<212> TYPE: DNA
<213> ORGANISM: Unknown

```
<220> FEATURE:
<223> OTHER INFORMATION: Description of Unknown:
      16S sequence

<400> SEQUENCE: 17
gaagtgcggt tcaacaccct ccg                                              23

<210> SEQ ID NO 18
<211> LENGTH: 15
<212> TYPE: DNA
<213> ORGANISM: Unknown
<220> FEATURE:
<223> OTHER INFORMATION: Description of Unknown:
      16S sequence

<400> SEQUENCE: 18
gatacagaga tgcat                                                       15

<210> SEQ ID NO 19
<211> LENGTH: 15
<212> TYPE: DNA
<213> ORGANISM: Unknown
<220> FEATURE:
<223> OTHER INFORMATION: Description of Unknown:
      16S sequence

<400> SEQUENCE: 19
gatacagtga tgcat                                                       15

<210> SEQ ID NO 20
<211> LENGTH: 15
<212> TYPE: DNA
<213> ORGANISM: Unknown
<220> FEATURE:
<223> OTHER INFORMATION: Description of Unknown:
      16S sequence

<400> SEQUENCE: 20
gatacagtag atgca                                                       15

<210> SEQ ID NO 21
<211> LENGTH: 15
<212> TYPE: DNA
<213> ORGANISM: Unknown
<220> FEATURE:
<223> OTHER INFORMATION: Description of Unknown:
      16S sequence

<400> SEQUENCE: 21
taccagattt acata                                                       15

<210> SEQ ID NO 22
<211> LENGTH: 15
<212> TYPE: DNA
<213> ORGANISM: Unknown
<220> FEATURE:
<223> OTHER INFORMATION: Description of Unknown:
      16S sequence

<400> SEQUENCE: 22
taccagatta catac                                                       15

<210> SEQ ID NO 23
<211> LENGTH: 14
<212> TYPE: DNA
<213> ORGANISM: Unknown
<220> FEATURE:
```

```
<223> OTHER INFORMATION: Description of Unknown:
      16S sequence

<400> SEQUENCE: 23
caggtaggat aata                                                    14

<210> SEQ ID NO 24
<211> LENGTH: 15
<212> TYPE: DNA
<213> ORGANISM: Unknown
<220> FEATURE:
<223> OTHER INFORMATION: Description of Unknown:
      16S sequence

<400> SEQUENCE: 24
caggtaggat aatta                                                   15

<210> SEQ ID NO 25
<211> LENGTH: 15
<212> TYPE: DNA
<213> ORGANISM: Unknown
<220> FEATURE:
<223> OTHER INFORMATION: Description of Unknown:
      16S sequence

<400> SEQUENCE: 25
caggtaggat aaata                                                   15

<210> SEQ ID NO 26
<211> LENGTH: 13
<212> TYPE: DNA
<213> ORGANISM: Unknown
<220> FEATURE:
<223> OTHER INFORMATION: Description of Unknown:
      16S sequence

<400> SEQUENCE: 26
caggtaggaa ata                                                     13

<210> SEQ ID NO 27
<211> LENGTH: 14
<212> TYPE: DNA
<213> ORGANISM: Unknown
<220> FEATURE:
<223> OTHER INFORMATION: Description of Unknown:
      16S sequence

<400> SEQUENCE: 27
gattacagat taca                                                    14

<210> SEQ ID NO 28
<211> LENGTH: 15
<212> TYPE: DNA
<213> ORGANISM: Unknown
<220> FEATURE:
<223> OTHER INFORMATION: Description of Unknown:
      16S sequence

<400> SEQUENCE: 28
gattacagat ttaca                                                   15

<210> SEQ ID NO 29
<211> LENGTH: 15
<212> TYPE: DNA
```

```
<213> ORGANISM: Unknown
<220> FEATURE:
<223> OTHER INFORMATION: Description of Unknown:
      16S sequence

<400> SEQUENCE: 29
gattacagaa ttaca                                                     15
```

METHODS AND COMPOSITIONS FOR TREATING SKIN DISEASE WITH RECOMBINANT MICROORGANISMS

RELATED APPLICATIONS

This application is a continuation of International Patent Application No. PCT/US2019/026045, filed Apr. 5, 2019, which claims priority to U.S. Provisional Patent Application No. 62/653,021, filed on Apr. 5, 2018, the entire contents of which are incorporated herein by reference for all purposes.

BACKGROUND OF THE INVENTION

Ichthyosis vulgaris (IV) is a chronic, xerotic, scaly skin disease with an estimated incidence and prevalence of 1 in 250,[1,2] which gives a total patient population of 1.3 million in the United States. Clinical features of IV usually appear at around 2 months of age and include generalized xerosis and fine, white to gray scales that are prominent on the abdomen, chest, and extensor surfaces of the extremities.[3] Some IV patients also experience hypohidrosis and heat intolerance.[4] The pathogenesis of IV has long been identified as a decrease in the size or number, or even a complete absence of, epidermal keratohyaline granules.[5-7] In addition, due to genetic factors, patients with IV are at increased risk for atopic dermatitis (AD), asthma, and allergies.[8]

Icthyosis vulgaris is an autosomal semidominant disease caused by loss-of-function mutations in the gene encoding filaggrin.[9] Filaggrin is an essential structural protein that is derived from profilaggrin, which breaks down into monomeric filaggrin in the stratum corneum and reinforces the skin barrier by binding to keratins and other intermediate filament proteins in the keratinocyte cytoskeleton.[10]

Many studies have identified loss-of-function mutations in FLG in IV and atopic dermatitis patients,[11-14] and these mutations are associated with disorganized keratin filaments, skin barrier defects[15] and microfractures in the stratum corneum leading to enhanced percutaneous allergen sensitization.[16-19] Moreover, filaggrin and its breakdown products have significant additional functions in the skin including moisturizing the skin (via hygroscopic amino acids or "natural moisturizing factors"),[20,21] effecting production of antimicrobial molecules (particularly against S. aureus),[22] and maintaining both a beneficial lipid profile[23,24] and pH[24-26] in the skin.

Current treatment options for IV include primarily topical water evaporation suppressants (e.g., sodium chloride, urea, lactic acid, salicylic acid), and moisturizers (e.g., glycerol, propylene glycol, dexpanthenol).[4] Topical retinoids may also be prescribed in an effort to slow the body's production of skin cells; however, as Vitamin A derivatives, long-term use is not ideal. Notably, many patients with IV experience a significantly reduced quality of life,[27-29] due to self-consciousness and social embarrassment, and see a negative impact on domestic life, educational/professional lives, and even leisure/sports activities.[28,29] It is clear that IV is a large, unmet need.

Diverse communities of microorganisms populate the skin, and a square centimeter can contain up to a billion microorganisms.[39] These diverse communities of bacteria, fungi, mites and viruses can provide protection against disease and form dynamic, yet distinct niches on the skin.[40] Increasing evidence has associated altered microbial communities or dysbiosis in the skin with cutaneous diseases,[39,41] especially AD.[42,43] Engineered probiotics are a novel approach based on leveraging the skin microbiome for therapeutic purposes. Notably, an engineered probiotic has important advantages over other methods of drug delivery, as it will establish residence on the patient's skin and continuously and stably deliver therapeutic proteins in situ. Furthermore, certain strains of Staphylococcus epidermidis (SE) have demonstrated important beneficial immunomodulatory and anti-pathogen effects in the skin, which are relevant to atopic dermatitis disease phenotype and severity. Moreover, the delivery of filaggrin, which is a structural protein derived from profilaggrin, further enhances the therapeutic approach due to filaggrin's role in the skin barrier and ability to reduce transepidermal water loss and improve skin hydration. The present invention has the surprising advantage of providing methods and compositions for treating skin diseases, e.g., atopic dermatitis, using a genetically engineered, recombinant strain of Staphylococcus epidermidis as a skin drug delivery system that secretes human filaggrin to address the pathophysiology of atopic dermatitis (e.g., AZT-01). Once applied to the skin, stable colonization of the skin and the subsequent secretion of filaggrin in situ can resolve the disease. The benefits of this invention include its safety as a non-steroidal treatment option, its efficacy due to the invention's combination of benefits from the secretion of filaggrin along with the benefits of the topical application of Staphylococcus epidermidis, and its ability to be therapeutically effective at even a low frequency of application (no more than once a day).

The present invention therefore addresses the long-felt need for an effective treatment for inflammatory skin diseases, and in particular, for IV. The present invention is also one of the first reported demonstrations of commensal skin bacteria that can secrete therapeutic proteins to treat skin disease.

SUMMARY OF THE INVENTION

The present disclosure features a novel treatment modality for skin disease, for example ichthyosis vulgaris (IV), that directly addresses the pathophysiology of ichthyosis vulgaris and consists of a live biotherapeutic product (LBP) comprised of human filaggrin-secreting Staphylococcus epidermidis. A goal of the present disclosure is to supplement the skin with long-term, stable delivery of filaggrin via a beneficial microbe-based chassis system. While the bacteria's potential probiotic properties are leveraged and optimized by the present invention, disease remediation is based on rational targeted expression of relevant proteins that directly address underlying pathophysiology. Additionally, because response to different microbial species and strains will differ between individuals, a modular design to control therapeutic delivery will likely provide significantly improved pharmacokinetics and disease resolution over current approaches that leverage naturally occurring strains. Importantly, the introduction of S. epidermidis could aid in re-establishing skin homeostasis by targeting pathogen-driven dysbiosis, as certain strains can secrete antimicrobial peptides.

Thus, the present invention relates, inter alia, to methods and compositions for treating skin diseases, for example IV, comprising an engineered microorganism capable of expressing therapeutically relevant recombinant fusion polypeptides (i.e. proteins, peptides, or amino acids).

The present invention features, in a first aspect, a recombinant microorganism capable of secreting a polypeptide, wherein the recombinant microorganism comprises an expression vector comprising a first coding sequence comprising a gene capable of expressing the polypeptide and a second coding sequence comprising a gene capable of expressing a cell penetrating peptide. In a related embodiment, the recombinant microorganism further comprising a third coding sequence comprising a gene capable of expressing an export signal. In yet another embodiment, the expression of the first coding sequence, second coding sequence and third coding sequence is under the control of a promoter. In other embodiments, the arrangement of the first coding sequence, second coding sequence and third coding sequences are in-frame. In yet another related embodiment, the first coding sequence, second coding sequence and third coding sequence are operably linked to a promoter. In one embodiment, the recombinant microorganism is bacteria, or a combination of bacteria. In another embodiment, the polypeptide is filaggrin, or a variant thereof. In other embodiments, the microorganism is selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus,* or combinations thereof. In other embodiments, the recombinant microorganism is *Staphylococcus epidermidis*. In some embodiments, the microorganism secretes a filaggrin fusion protein. In a further embodiment, the filaggrin fusion protein comprises an amino acid sequence that is 85%, 86%, 87%, 88%, 89%, 90%, 91%, 92%, 93%, 94%, 95%, 96%, 97%, 98%, or 99% identical to SEQ ID NO. 1. In one embodiment, the filaggrin fusion protein consists of SEQ ID NO: 1.

The present invention features, in a further aspect, a method for producing a live biotherapeutic composition, the method comprising (a) transfecting a cell with (i) a first coding sequence comprising a nucleic acid sequence capable of expressing a therapeutic polypeptide, and (ii) a second coding sequence comprising a nucleic acid sequence capable of expressing a cell penetrating peptide; and (b) allowing the transfected cell to produce a therapeutic polypeptide fusion protein; and (c) obtaining the live biotherapeutic composition. In a related embodiment, the method further comprises (iii) transfecting the cell with a third coding sequence comprising a nucleic acid sequence capable of expressing an export signal. In another embodiment, the first coding sequence, second coding sequence and third coding sequences are arranged in a single plasmid. In yet another embodiment, the arrangement of the first coding sequence, second coding sequence and third coding sequences are operably linked to a promoter. In other embodiments, the cell is selected from the group consisting of wherein the microorganism is selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus,* or combinations thereof. In yet another embodiment, the cell is *Staphylococcus epidermidis*. In other embodiments, the therapeutic polypeptide fusion protein is a filaggrin fusion protein, or a variant thereof. In a further embodiment, the filaggrin fusion protein comprises an amino acid sequence that is 85%, 86%, 87%, 88%, 89%, 90%, 91%, 92%, 93%, 94%, 95%, 96%, 97%, 98%, or 99% identical to SEQ ID NO. 1. In one embodiment, the filaggrin fusion protein consists of SEQ ID NO: 1.

In another aspect, the disclosure features a composition comprising a filaggrin polypeptide, or a variant thereof. In one embodiment, the filaggrin polypeptide is a fusion protein. In a further embodiment, the filaggrin fusion protein comprises an amino acid sequence that is 85%, 86%, 87%, 88%, 89%, 90%, 91%, 92%, 93%, 94%, 95%, 96%, 97%, 98%, or 99% identical to SEQ ID NO. 1. In one embodiment, the filaggrin fusion protein consists of SEQ ID NO: 1.

The present invention features, in a further aspect, a composition obtained by any one of the method disclosed or described herein. In a related embodiment, the composition comprises a pharmaceutically acceptable carrier, wherein the pharmaceutically acceptable carrier is selected from the group consisting of an aqueous solution, an emulsion, a cream, a lotion, a gel, or an ointment.

The present invention features, in a further aspect, a live biotherapeutic composition comprising a recombinant microorganism wherein the recombinant microorganism comprises (i) a first coding sequence comprising a nucleic acid sequence capable of expressing a therapeutic polypeptide; (ii) a second coding sequence comprising a nucleic acid sequence capable of expressing a cell penetrating peptide; (iii) a third coding sequence comprising a nucleic acid sequence capable of expressing an export signal; and (iv) a promoter operably linked to the first coding sequence, the second coding sequence and the third coding sequence; wherein the first coding sequence, second coding sequence and first coding sequence is capable of expressing a filaggrin fusion protein, or variant thereof. In a further embodiment, the filaggrin fusion protein comprises an amino acid sequence that is 85%, 86%, 87%, 88%, 89%, 90%, 91%, 92%, 93%, 94%, 95%, 96%, 97%, 98%, or 99% identical to SEQ ID NO. 1. In a related embodiment, the recombinant microorganism is *Staphylococcus epidermidis*. In a further embodiment, the export signal exports the filaggrin fusion product, or variant thereof, out of the recombinant microorganism. In yet another embodiment, the cell penetrating peptide facilitates the entry of the filaggrin fusion product, or variant thereof, into a human keratinocyte. In another embodiment, the composition comprises a pharmaceutically acceptable carrier, wherein the pharmaceutically acceptable carrier is selected from the group consisting of an aqueous solution, an emulsion, a cream, a lotion, a gel, or an ointment.

The present invention features, in a further aspect, a kit comprising any one of the compositions disclosed or described herein and instructions for use.

The present invention features, in a further aspect, a method of treating a skin disease comprising administering to a subject in need thereof the composition of any one of the compositions disclosed or described herein. In one embodiment, the skin disease is IV. In another embodiment, the skin disease is atopic dermatitis.

BRIEF DESCRIPTION OF THE DRAWINGS

FIG. 1 is a graph that shows characterization of growth strains in liquid culture. SE alone (solid black line, triangle markers) grew more quickly than SE-GFP alone or SE and SE-GFP together.

FIG. 2A-FIG. 2C shows characterization of growth of strains in RHE. FIG. 2A shows SE with empty vector (i.e. no protein production). FIG. 2B shows SE-GFP alone on RHE shows slower growth at 24 hours. FIG. 2C shows when mixed together 50:50 on RHE, SE empty vector outcompetes SE-GFP.

FIG. 3A-FIG. 3C shows fluorescence and reflective overlays. FIG. 3A shows fluorescent SE on the surface and outlining individual cells in the stratum corneum (dotted line shows outlines of corneocytes as an example).

FIG. 4A-FIG. 4C shows the results of purifying GFP. Protein was purified from 225 mL culture of SE (2.7-2.9 OD/mL) and lysed with CellB-Lyse (Sigma). 4 mL eluate was produced and ran on a Ni-NTA column in a buffer of PBS pH 7.4 and yielded 0.4 mg. FIG. 4A and FIG. 4B InVision His-tag stain on an SDS-PAGE gel with purified protein from SE. Lanes (1) lysate pellet; (2) supernatant, clarified; (3) pass-through; (4) eluate; (5) concentrate; (6) marker; (7) supernatant, clarified; (8) pass-through; (9) eluate; and (10) concentrate. FIG. 4C shows purified GFP from SE.

FIG. 5A-FIG. 5O shows characterization of the protein with and without the RMR signal using 5 μg GFP as a reporter in RHE. (FIG. 5A-FIG. 5D) Two-photon images of topically applied GFP with (FIG. 5C, FIG. 5D) or without (FIG. 5A, FIG. 5B) the RMR signal at 30 minutes (FIG. 5A, FIG. 5C, FIG. 5E, FIG. 5G) or 60 minutes (B,D,F,H). Images are compiled Z-stacks projected onto a 2D plane. (FIG. 5O) RHE punctured with Dermaroller microneedle with 50 ug GFP-RMR. Images taken 30 minutes after application.

FIG. 6A-FIG. 6F shows preliminary bioinformatics analyses of human filaggrin. (FIG. 6A) homology of human filaggrin domains. (FIG. 6B) sequence alignment of human filaggrin domains (SEQ ID NOS 4-14, respectively, in order of appearance). (FIG. 6C) hydrophobicity plot of the human filaggrin domains with a corresponding diagram of the filaggrin sequence. (FIG. 6D) Example SAR exercise for human filaggrin simians 9-10 using a hydrophobicity plot to remove QSGEnSGRnSFLYQVSnHEQSES (SEQ ID NO: 3) repeats at the N-terminus of hFLG 9-10 and (FIG. 6E) resulting sequence of this protein with RMR cell penetrating peptide added (SEQ ID NO: 15). (FIG. 6F) shows an overview of filaggrin structure. Part A (Top) shows profilaggrin and filaggrin gene structure. The majority of filaggrin is encoded by exon 3. Part B (Bottom) shows profilaggrin protein structure.

FIG. 7A-FIG. 7E shows assay development. (FIG. 7A-FIG. 7C) Western blots of hFLG in the media isolate from filaggrin-producing SE culture with various antibodies. (FIG. 7A) Sigma polyclonal anti-hFLG antibody. (FIG. 7B) SantaCruz polyclonal anti-hFLG antibody. (FIG. 7C) polyclonal anti-hFLG antibody. (FIG. 7D) Proposed workflow for method development of MS-based filaggrin detection. (FIG. 7E) Identity of expressed human filaggrin from mass spectrometry for hFLG9-10 (SEQ ID NO: 16). Colors indicate sequence confidence: dark blue (very high confidence), light blue (observed) and red (not observed).

FIG. 11 discloses SEQ ID NOS 17-20, 20-22, 22-23, 23-29, respectively, in order of appearance.

DETAILED DESCRIPTION OF THE INVENTION

Figure 2A:
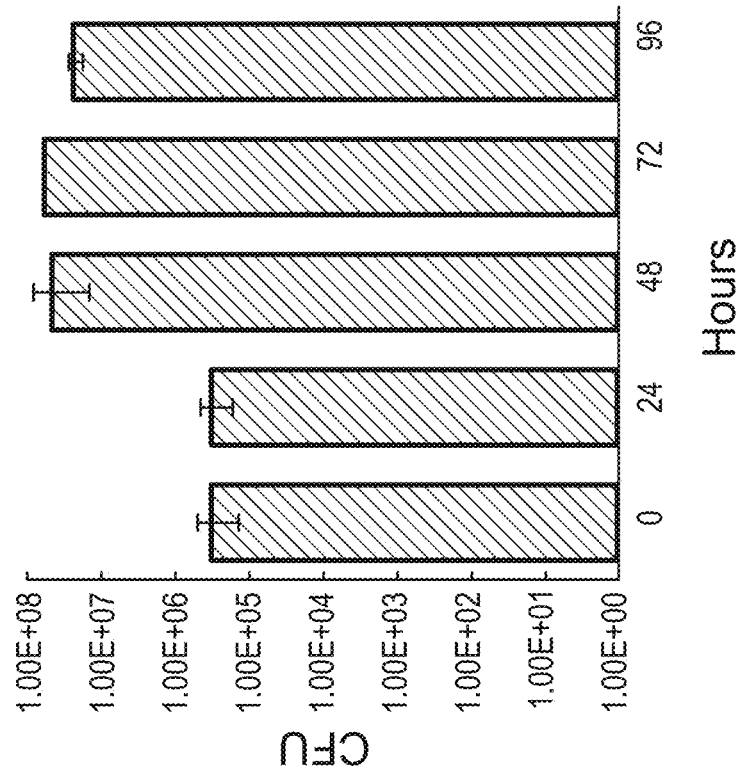

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "carriers", "carrier system" or "vehicles" refer to compatible substances that are suitable for delivering, containing, or "carrying" a pharmaceutical active ingredient or other materials for administration in a topically applied composition to a patient or subject. Carriers useful herein should be pharmaceutically acceptable. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue. Further examples of "carriers" include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers.

As used herein, the term "engineered bacterial strain," or a "recombinant bacterial strain" refers to a strain of bacteria that has been "genetically modified" or "engineered" by the introduction of DNA prepared outside the organism into the bacterial strain. For example, the introduction of a plasmid containing new genes or other nucleic acid sequence(s) into bacteria will allow the bacteria to express those genes or other nucleic acid sequence(s). Alternatively, the plasmid containing new genes or other nucleic acid sequence(s) can be introduced to the bacteria and then integrated into the bacteria's genome, where the bacteria will express those genes or other nucleic acid sequence(s).

As used herein, the term "host cell" is meant to refer to a cell which has been transformed or transfected, or is capable of transformation or transfection by an exogenous polynucleotide sequence.

The term "isolated" for the purposes of the present disclosure designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

An "isolated nucleic acid molecule" (such as, for example, an isolated promoter) is one which is separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule in the genomic DNA of the organism from which the nucleic acid molecule is derived.

As used here, the term "genetic element" is meant to refer to a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

As used here, the term "live biotherapeutic product" (or LBP) refers to a product candidate(s) containing bacteria, yeast, and/or other microorganisms.

As used herein, the terms "patient" or "subject", refers to a human or animal (in the case of an animal, more typically a mammal such as domesticated mammals, or animals such as poultry animals and fish and other seafood or freshwater food creatures), that would be subjected to the treatments and compositions of the present invention.

As used herein, the expression "a subject in need thereof" means a human or non-human animal that exhibits one or more symptoms or indicia of atopic dermatitis, and/or who has been diagnosed with IV.

As used herein, the phrase "pharmaceutically acceptable" refers to those active compounds, materials, engineered bacterial strain or strains, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

As used herein, the term "polynucleotide(s)" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. The term polynucleotide also embraces short polynucleotides often referred to as oligonucleotide(s). "Polynucleotide" and "nucleic acid" are often used interchangeably herein.

As used herein, the terms "polypeptide" or "protein" refer to biological molecules, or macromolecules composed of amino-acid residues bonding together in a chain. The definition of polypeptides used herein is intended to encompass proteins (generally higher molecular weight) composed of one or more long chains of amino acid residues and small peptides (generally lower molecular weight) of a few amino acids. In other embodiments, a single amino acid, although not technically a polypeptide, is also considered within the scope of the disclosure.

As used herein, the term "preventing", refers to completely or almost completely stopping an abnormal skin condition (e.g. IV) from occurring, for example when the patient or subject is predisposed to an abnormal skin condition or at risk of contracting an abnormal skin condition. Preventing can also include inhibiting, i.e. arresting the development, of an abnormal skin condition.

As used herein, a "promoter" is meant to refer to a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. For example, a promoter may be regulated in a tissue-specific manner such that it is only active in transcribing the associated coding region in a specific tissue type(s).

As used herein, the term "reducing the risk of", refers to lowering the likelihood or probability of an abnormal skin condition (e.g. IV) from occurring, for example when the patient or subject is predisposed to an abnormal skin condition or at risk of contracting an abnormal skin condition.

As used herein, the term "therapeutically effective amount" refers to an amount of a pharmaceutical active compound, or a combination of compounds, or an amount of pharmaceutical active compound delivered by an engineered bacterial strain or strains, for example a skin treatment agent or agents, when administered alone or in combination, to treat, prevent, or reduce the risk of a disease state or condition, for example an abnormal skin condition (e.g. IV). The term also refers to an amount of a pharmaceutical composition containing an active compound or combination of compounds or an engineered bacterial strain or strains that delivers a pharmaceutical active compound. For example, an effective amount refers to an amount of the compound or an amount of the compound delivered by an engineered bacterial strain or strains present in a formulation given to a recipient patient or subject sufficient to elicit biological activity, for example, activity for treating or preventing an abnormal skin condition.

Figure 2B:
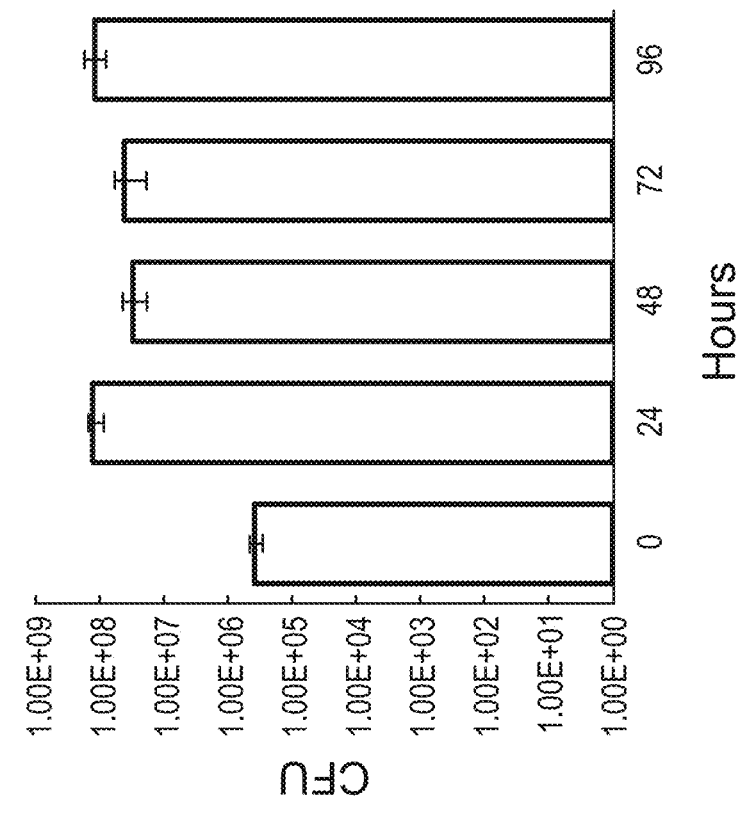

As used herein, the term "treating" refers to providing a therapeutic intervention to cure or ameliorate an abnormal skin condition (e.g. IV Compositions The present invention provides skin-colonizing microorganisms, e.g., bacteria, that are genetically altered to express recombinant therapeutic polypeptides for the treatment or prevention of skin disease (FIG. 2). Using genetically engineered protein-producing microorganisms, e.g., bacteria, has several advantages over the prior art method of treating skin disease. Therapeutic proteins are able to treat the underlying cause of defects leading to the skin condition. Further, microorganisms, e.g., bacteria, are able to self-replicate while retaining the inserted nucleic acid (e.g., a gene) to continuously produce the therapeutic protein.

The present invention provides skin-colonizing microorganisms, e.g., bacteria, such as for example, Staphylococcus epidermidis, that are genetically altered to express therapeutic proteins, e.g., human filaggrin. Using genetically engineered filaggrin-producing microorganisms, e.g., bacteria, has several advantages over using filaggrin supplementation. First, microorganisms, e.g., bacteria, are able to self-replicate while retaining the inserted filaggrin nucleic acid sequence (e.g., a gene). Second, S. epidermidis is normally present on the skin and has been shown to inhibit growth of Staphylococcus aureus, a bacterial species of the same genre that dominates the skin flora in atopic dermatitis flares.

Bacterial Strains

The present invention provides genetically altered microorganisms, e.g., bacteria, capable of expressing recombinant therapeutic proteins. A wide range of microorganisms are suitable for use in the present invention. Examples include, but are not limited to, non-pathogenic and commensal bacteria. Bacteria suitable for use in the present invention include, but are not limited to, *Bifidobacterium, Brevibacterium, Propionibacterium, Lactococcus, Streptococcus, Staphylococcus* (e.g., *S. epidermidis*), *Lactobacillus* (e.g., *L. acidophilus*), *Pediococcus, Leuconostoc,* or *Oenococcus*. In certain embodiments of the invention, the bacterium is *Staphylococcus epidermidis*. In preferred embodiments of the invention, the strain of *S. epidermidis* to be used is incapable of producing biofilms. One such example of a strain of *S. epidermidis* incapable of producing biofilms is *S. epidermidis* strain ATCC 12228. However, in yet other embodiments of the invention, other related or similar species found on the skin can be used.

Therapeutic Proteins

The present invention provides genetically altered microorganisms, e.g., bacteria, capable of expressing recombinant therapeutic proteins. In preferred embodiments of the invention, the therapeutic protein comprises human filaggrin. Human filaggrin is expressed by a human gene encoding filaggrin (FLG). Filaggrin is a protein produced by differentiating keratinocytes and functions to aggregate keratin filaments into a cytoskeleton, which, in combination with other components, comprises the cornified cell envelope. FLG is a large gene located on chromosome lq21 that produces profilaggrin, an insoluble polyprotein that is proteolyzed to release functional filaggrin monomers (Armengot-Carbo et al. 2014). The therapeutic protein (and, i.e., the gene from which the protein is expressed) of the invention may be from any mammal. Non-limiting examples include, but are not limited to, mouse, rat, rabbit, goat, sheep, horse, cow, dog, primate, or human gene sequence. In preferred embodiments of the invention, the therapeutic protein comprises a recombinant fusion protein comprising filaggrin operably linked to a cell penetrating protein (CPP). In one embodiment, the cell penetrating protein is RMRRMRRMRR (SEQ ID NO: 2). In other embodiments of the invention, the therapeutic protein comprises a recombinant fusion protein comprising filaggrin operably linked to an export or secretion signal, which allows the recombinant filaggrin to be exported out of the microorganism (e.g., bacteria). In another embodiment, the therapeutic protein comprises a recombinant fusion protein comprising filaggrin operably linked to a cell penetrating protein (CPP) and to an export or secretion signal.

In one embodiment, the fusion protein comprising filaggrin operably linked to a cell penetrating protein is shown in SEQ ID NO. 1

```
                                                                 SEQ ID NO. 1
                                                        1430           1440
                                                        MQ    SGESSGRSRS 1450        1460        1470        1480        1490        1500
     FLYQVSSHEQ  SESTRGQTAT  STGGRQGSRS  EQARNSSRHS  ASQDGQDTIR  GHPGSSRGGR 1510        1520        1530        1540        1550        1560
     QGSYNEQSVD  RSGHSGYHHS  HTTPQGRSDA  SHGQSGPRSA  SRQTRNEEQS  GDGSRHSGSR 1570        1580        1590        1600        1610        1620
     HHEPSTRAGS  SRHSQVGQGE  SAGSKTSRRQ  GSSVSQDRDS  EGHSEDSERR  SESASRNHYG 1630        1640        1650        1660        1670        1600
     SAREQSRHGS  RNPRSHQEDR  ASHGHSAESS  RQSGTRHAET  SSGGQAASSQ  EQARSSPGER 1690        1700        1710        1720        1730        1740
     HGSRHQQSAD  SSTDSGTGRR  QDSSVVGDSS  NRGSSGSQAS  DSEGHSEESD  TQSVSAHGQA 1750        1760        1770
     GPHQQSHQES  TRGQSGERSG  RSGSFLYQVS  THEQSESRMR  RMRRMRR
```

In one embodiment, the filaggrin fusion protein comprises an amino acid sequence that is 85%, 86%, 87%, 88%, 89%, 90%, 91%, 92%, 93%, 94%, 95%, 96%, 97%, 98%, or 99% identical to SEQ ID NO. 1. In one embodiment, the filaggrin fusion protein consists of SEQ ID NO: 1.

In some aspects, the therapeutic protein is not expressed by a microorganism (e.g. a bacteria). In some aspects, the therapeutic protein comprises a filaggrin polypeptide, or a variant thereof. In one embodiment, the filaggrin polypeptide is a fusion protein. In a further embodiment, the filaggrin polypeptide comprises an amino acid sequence that is 85%, 86%, 87%, 88%, 89%, 90%, 91%, 92%, 93%, 94%, 95%, 96%, 97%, 98%, or 99% identical to SEQ ID NO. 1. In one embodiment, the filaggrin fusion protein consists of SEQ ID NO: 1.

Secretion Signals

Secretion signals or export signals are peptide sequences on a protein that facilitate the export of the protein through the secretory pathway, which ultimately results in the protein being secreted from the cell. In the present invention, any secretion signal that facilitates the export of a protein, such as a protein comprising filaggrin, out of a microorganism (e.g., a bacterial cell) is contemplated as a secretion signal.

Cell Penetrating Peptides

A cell penetrating peptide is a peptide sequence that facilitates or mediates the delivery of a biomolecule (e.g., a protein) in vivo without using any receptors and without causing any significant membrane damage. Cell penetrating peptides that facilitate entry into the skin keratinocytes are contemplated as a cell penetrating peptides of the present invention.

In one embodiment, the cell penetrating protein is RMRRMRRMRR (SEQ ID NO. 2).

Genetic Construct

The present invention utilizes standard molecular biology techniques, e.g., those described in (Sambrook et al. 2001). An example of the genetic construct used for this invention is pAZT, which is based on pJB38, an allelic exchange *E. coli*-staphylococcal shuttle vector, further comprising additional design features on the plasmid to improve functionality (Bose, J. L., et al. *Applied and environmental microbiology.* 2013; 79(7):2218-2224). The plasmid is constructed by inserting cDNA of a gene encoding a therapeutic protein into a restriction site, using standard molecular biology techniques (FIG. 2). The insert further comprises a coding sequence driven by a promoter. Such a promoter can be either constitutive or inducible. Examples of inducible promoters include those that are activated by chemical compounds such as alcohols, sugars, metals, or tetracycline, or by physical factors such as light or high temperatures.

The mRNA sequence of human FLG has a Genebank accession No. NM_002016. A plasmid pAZT was constructed by inserting part of the FLG cDNA into a restriction site of pJB38. The insert contains a nucleic acid coding sequence driven by a promoter. The construct further comprises a nucleic acid sequence encoding a secretion signal and a cell penetrating peptide, thus resulting in a recombinant filaggrin fusion protein.

Uses of Recombinant Bacterial Strain

It will be understood that the skin disease to be treated can be any disease or disorder associated with skin. In one embodiment the disorder is selected from the group consisting of atopic dermatitis, psoriasis, acne, allergic contact dermatitis, epidermolytic hyperkeratosis, seborrheic dermatitis, eczema, dry skin, allergy, rashes, UV-irritated skin, detergent irritated skin (including irritation caused by enzymes and compounds used in washing detergents and sodium lauryl sulfate), thinning skin (e.g. skin from the elderly and children), bullous pemphigoid, pemphigus vulgaris, impetigo, vitiligio, baldness, and hirsutism. In one particular embodiment, the skin disease is Ichthyosis vulgaris (IV).

Examples of proteins that can be administered according to the invention are preferably eukaryotic proteins. These proteins include, but are not limited to, single amino acids, small peptides, and large proteins. More particularly, genes encoding proteins that are useful in the invention as recombinant therapeutic proteins include, but are not limited to, the following: members of the interleukin family of genes, including, but not limited to, IL-2, IL-3, IL-4, IL-5, IL-6, IL-7, IL-8, IL-9, IL-10, IL-11, IL-12, IL-13, IL-14 and IL-15 and genes encoding receptor antagonists thereof. Genes which encode hematopoietic growth factors, including but not limited to, erythropoietin, granulocyte colony stimulating factor, granulocyte macrophage colony stimulating factor, macrophage colony stimulating factor, stem cell factor, leukemia inhibitory factor and thrombopoietin are also contemplated in the invention. Genes encoding neurotropic factors are also contemplated, including but not limited to, nerve growth factor, brain derived neurotropic factor and ciliary neurotropic factor. In addition, genes which encode interferons, including, but not limited, to IFN-alpha, IFN-beta and IFN-gamma are included. Further contemplated in the present invention are genes encoding chemokines such as the C—C family and the C—X—C family of cytokines, genes encoding hormones, such as proinsulin and growth hormone, and genes encoding thrombolytic enzymes, including tissue plasminogen activator, streptokinase, urokinase or other enzymes such as trypsin inhibitor. The invention further includes genes which encode tissue repair factors, growth and regulatory factors including, but not limited to, oncostatine M, platelet-derived growth factors, fibroblast growth factors, epidermal growth factor, hepatocyte growth factor, bone morphogenic proteins, insulin-like growth factors, calcitonin and transforming growth factor alpha and beta. Further contemplated genes include genes encoding structural proteins including filaggrin, actin, collagen, fibrillin, elastin, or scleroprotein.

In particular embodiments, the gene is a gene encoding filaggrin.

Antibodies

Also provided in the present disclosure is an antibody against an epitope of hFLG that is common across all pairs of subdomains. In certain embodiments, the antibody is a chicken IgY.

Formulations

A formulation for use according to the present invention may comprise any pharmaceutically effective amount of a genetically engineered microorganism, e.g., bacteria, to produce a therapeutically effective amount of a desired polypeptide, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about. 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% or more by weight of the genetically engineered microorganism, e.g., bacteria, the upper limit of which is about 90.0% by weight of the genetically engineered microorganism, e.g., bacteria.

In an alternative embodiment, the formulation for use according to the present invention can comprise, for example, at least about 0,01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0,3% to about 5%, about 0.4% to about 5%, about 0.5% to about 5%, about 1% to about 5%, or more by weight of a genetically engineered microorganism, e.g., bacteria.

In some aspects, a formulation for use according to the present invention may comprise any pharmaceutically effective amount of a filaggrin polypeptide, or a variant thereof. In one embodiment, the filaggrin polypeptide is a fusion protein. In a further embodiment, the filaggrin polypeptide comprises an amino acid sequence that is 85%, 86%, 87%, 88%, 89%, 90%, 91%, 92%, 93%, 94%, 95%, 96%, 97%, 98%, or 99% identical to SEQ ID NO. 1.

In some embodiments, the formulation is a topical formulation. The topical formulation for use in the present invention can be in any form suitable for application to the body surface, such as a cream, lotion, sprays, solution, gel, ointment, paste, plaster, paint, bioadhesive, suspensions, emulsions, or the like, and/or can be prepared so as to contain liposomes, micelles, and/or microspheres. Such a formulation can be used in combination with an occlusive overlayer so that moisture evaporating from the body surface is maintained within the formulation upon application to the body surface and thereafter. The formulation can include a living biotherapeutic composition and can comprise at least one a genetically engineered microorganism, e.g., an engineered bacterial strain, that produces a recombinant polypeptide. This engineered living biotherapeutic composition can deliver the polypeptide directly to the skin for treating or preventing abnormal skin conditions, and/or skin diseases (e.g., inflammatory skin diseases).

Topical formulations include those in which any other active ingredients are dissolved or dispersed in a dermatological vehicle known in the art, e.g. aqueous or nonaqueous gels, ointments, water-in-oil or oil-in-water emulsions. Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending upon the nature of the formulation as well as its intended use and site of application, the dermatological vehicle employed can contain one or more components (e.g., when the formulation is an aqueous gel, components in addition to water) selected from the following: a solubilizing agent or solvent (e.g. a β-cyclodextrin, such as bydroxypropyl β-cyclodextrin, or an alcohol or polyol such as ethanol, propylene glycol or glycerol); a thickening agent (e.g. hydroxyethylceliulose, hydroxypropylcellulose, carboxymethylcellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (such as a mixture of dihydrogen phosphate and hydrogen phosphate salts, or a mixture of citric acid and a hydrogen phosphate salt).

A pharmaceutically acceptable carrier can also be incorporated in the formulation of the present invention and can be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers.

The term "pharmaceutically acceptable" or "pharmaceutically acceptable carrier" is used herein to refer to a compound or composition that can be incorporated into a pharmaceutical formulation without causing undesirable biological effects or unwanted, interaction with other components of the formulation, "carriers" or "vehicles" as used herein refer to carrier materials suitable for incorporation in a topically applied composition. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue.

Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semiliquid preparations in which particles, including the active agent, are present in a water or alcohol base. Lotions are usually suspensions of solids, and preferably, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like. Solutions are homogeneous mixtures prepared by dissolving one or more chemical substances (solutes) in a liquid such that the molecules of the dissolved substance are dispersed among those of the solvent. The solution can contain other pharmaceutically or cosmetically acceptable chemicals to buffer, stabilize or preserve the solute. Common examples of solvents used in preparing solutions are ethanol, water, propylene glycol or any other acceptable vehicles. As is of course well known, gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred organic macromolecules, i.e., gelling agents, are cross-linked acrylic acid polymers such as the "carbomer" family of polymers, e.g., carboxypolyalkylenes that can be obtained commercially under the Carbopol trademark. Also preferred are hydrophilic polymers such as polyethylene oxides, polyoxyethylene-polyoxypropylene copolymers and polyvinylalcohol; cellulosic polymers such as hydroxy-propyl cellulose, hydroxyethyl cellulose, hydroxypropyl methylcellulose, hydroxy-propyl methylcellulose phthalate, and methylcellulose; gums such as tragacanth and xanthan gum; sodium alginate; and gelatin, In order to prepare a uniform gel, dispersing agents such as alcohol or glycerin can be added, or the gelling agent can be dispersed by trituration, mechanical mixing or stirring, or combinations thereof. Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, PA: Mack Publishing Co., 1995), at pages 1399-1404, ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum.

Emulsifiable ointment bases, also known as absorbent ointment bases, contain little or no water and include, for example, hydroxystearin sulfate, anhydrous lanolin, and hydrophilic petrolatum.

Emulsion ointment bases are either water-in-oil (W/O) emulsions or oil-in-water (O/W) emulsions, and include, for example, acetyl alcohol, glyceryl monostearate, lanolin, and stearic acid. Preferred water-soluble ointment bases are prepared from polyethylene glycols of varying molecular weight; see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Enhancers are lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter $\delta$ of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol nionolaurace, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a C2-C4 alkane diol or triol, are substituted with one or two fatty ether substituents. Additional permeation enhancers will be known to those of ordinary skill in the art of topical drag delivery, and/or are described in the pertinent texts and literature. See, e.g., Percutaneous Penetration Enhancers, eds. Smith et al. (CRC Press, 1995)(incorporated herein by reference herein in its entirety).

Various other additives can be included in the compositions of the present invention in addition to those identified above. These include, but are not limited to, antioxidants, astringents, perfumes, preservatives, emollients, pigments, dyes, humectants, propellants, and sunscreen agents, as well as other classes of materials whose presence can be pharmaceutically or otherwise desirable. Typical examples of optional additives for inclusion in the formulations of the present invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylaury 1 ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), a-tocopherol (Vitamin E), $\beta$-tocopherol, $\gamma$-tocopherol, $\delta$-tocopherol, $\epsilon$-tocopherol, $\zeta_1$-tocopherol, $Z^A$-tocopherol, $\eta$-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that can be obtained commercially under the Carbopol trademark. Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (Vitamin C), a-tocopherol (Vitamin E), $\beta$-tocopherol, $\gamma$-tocopherol, $\delta$-tocopherol, $\epsilon$-tocopherol, $\zeta_1$-tocopherol, $\zeta_2$-tocopherol, $\eta$-tocopherol, and retinol (Vitamin A), and/or pharmaceutically acceptable salts, esters, amides, or other derivatives thereof. A preferred tocopherol compound is a-tocopherol. Additional agents include those that are capable of improving oxygen supply in skin tissue, as described, for example, in Gross, et al., WO 94/00098 and Gross, et al., WO 94/00109, both assigned to Lancaster Group AG (incorporated herein by reference in their entirety). Sunscreens and UV absorbing compounds can also be included. Non-limiting examples of such sunscreens and UV absorbing compounds include aminobenzoic acid (PABA), avobenzone, cinoxate, dioxybenzone, homosalate, menthyl anthranilate, oxtocrylene, octyl methoxycmnamate, octyl salicylate, oxybenzone, padirnate O, phenylbenzirmdazole sulfonic acid, sulisobenzone, titanium dioxide, trolamine salicylate, zinc oxide, ensulizole, meradiraate, octinoxate, octisalate, and octocrylene. See Title 21. Chapter 1. Subchapter D. Part 352. "Sunscreen drug products for over-the-counter human use" incorporated herein in its entirety. Other embodiments can include a variety of non-carcinogenic, non-irritating healing materials that facilitate treatment with the formulations of the invention. Such healing materials can include nutrients, minerals, vitamins, electrolytes, enzymes, herbs, plant extracts, glandular or animal extracts, or safe therapeutic agents that can be added to the formulation to facilitate the healing of dermal disorders.

The present invention contemplates amounts of these various additives equivalent to those conventionally used in the cosmetics field, and range, for example, from about 0.01% to about 20% of the total weight of the topical formulation.

The formulations of the invention can also include conventional additives such as opacifiers, fragrance, colorant, stabilizers, surfactants, and the like. In certain embodiments, other agents can also be added, such as antimicrobial agents, to prevent spoilage upon storage, i.e., to inhibit growth of microbes such as yeasts and molds.

Suitable antimicrobial agents for the present invention include, but are not limited to the following selected from the group consisting of the methyl and propyl esters of p-hydroxybenzoic acid (i.e., methyl and propyl paraben), sodium benzoate, sorbic acid, imidurea, and combinations thereof. In other embodiments, other agents can also be added, such as repressors and inducers, i.e., to inhibit (i.e., glycose) or induce (i.e. xylose) the production of the polypeptide of interest. Such additives can be employed provided they are compatible with and do not interfere with the function of the formulations.

The formulations can also contain irritation-mitigating additives to minimize or eliminate the possibility of skin irritation or skin damage resulting from the chemical entity to be administered, or other components of the composition.

Suitable irritation-mitigating additives include, for example: a-tocopherol; monoamine oxidase inhibitors, particularly phenyl alcohols such as 2-phenyl-1-ethanol; glycerin; salicylates; ascorbates; ionophores such as monensin; amphophilic amines; ammonium chloride; N-acetylcysteine; capsaicin; and chloroquine. The irritation-mitigating additive, if present, can be incorporated into the compositions at a concentration effective to mitigate irritation or skin damage, typically representing not more than about 20 wt. %, more typically not more than about 5 wt. %, of the formulation. Further suitable pharmacologically active agents that can be incorporated into the present formulations in certain embodiments and thus topically applied along with the active agent include, but are not limited to, the following: agents that improve or eradicate pigmented or non-pigmented age spots, keratoses, and wrinkles; antimicrobial agents; antibacterial agents; antipruritic and antixerotic agents; anti-inflammatory agents; local anesthetics and analgesics; corticosteroids; retinoids; vitamins; hormones; and antimetabolites. Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycmnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil. A cream, lotion, gel, ointment, paste or the like can be spread on the affected surface and gently rubbed in. A solution can be applied in the same way, but more typically will be applied with a dropper, swab, or the like, and carefully applied to the affected areas.

The application regimen will depend on a number of factors that can readily be determined, such as the severity of the condition and its responsiveness to initial treatment, but will normally not involve more than one application per day. One of ordinary skill can readily determine the optimum amount of the formulation to be administered, administration methodologies and repetition rates. In general, it is contemplated that the formulations of the invention will be applied in the range of once or twice weekly up to once daily.

Methods
Methods of Treatment

The invention provides methods for treating a skin disease, wherein the methods comprise administering to a subject in need of such treatment a genetically engineered microorganism, e.g., genetically engineered bacteria, capable of expressing a recombinant therapeutic fusion protein of the invention, thereby treating the subject. In some aspects, the invention provides methods for treating a skin disease, wherein the methods comprise administering to a subject in need of such treatment a pharmaceutical composition comprising a filaggrin polypeptide described herein. In some embodiments, the filaggrin polypeptide is a fusion protein. In a further embodiment, the filaggrin polypeptide comprises an amino acid sequence that is 85%, 86%, 87%, 88%, 89%, 90%, 91%, 92%, 93%, 94%, 95%, 96%, 97%, 98%, or 99% identical to SEQ ID NO. 1.

In one embodiment, the disease is atopic dermatitis.

In one embodiment, the disease is Ichthyosis vulgaris (IV). Clinical features of IV usually appear at around 2 months of age and include generalized xerosis and fine, white to gray scales that are prominent on the abdomen, chest, and extensor surfaces of the extremities. IV is commonly caused by a genetic mutation that's inherited from one or both parents. The scales of ichthyosis vulgaris, sometimes called fish scale disease or fish skin disease, can be present at birth, but usually first appear during early childhood. In one embodiment, the subject to be treated is a child. Sometimes other skin diseases, such as the allergic skin condition eczema, are associated with ichthyosis vulgaris.

In yet another preferred embodiment, the recombinant therapeutic fusion protein comprises filaggrin. In other embodiments, the recombinant therapeutic fusion protein comprises filaggrin operably linked to a cell penetrating peptide. In one embodiment, the filaggrin fusion protein comprises an amino acid sequence that is 85%, 86%, 87%, 88%, 89%, 90%, 91%, 92%, 93%, 94%, 95%, 96%, 97%, 98%, or 99% identical to SEQ ID NO. 1.

In further embodiments, the recombinant therapeutic fusion protein is operably linked to an export signal.

Kits

The present invention also provides kits. In one aspect, a kit of the invention comprises (a) a composition of the invention and (b) instructions for use thereof. In another aspect, a kit of the invention comprises (a) any one of the live biotherapeutic compositions of the invention, and (b) instructions for use thereof. The compositions of the invention are described supra. In some embodiments, a composition of the invention is an engineered microorganism capable of expressing therapeutically relevant recombinant fusion polypeptides, as described supra. In preferred embodiments, the composition comprises engineered bacteria (e.g., *S. epidermidis*) capable of expressing a recombinant fusion polypeptide comprising filaggrin.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1. Quantification and Comparison of Growth Characteristics of Transformed Bacteria in Liquid Media It was important to gain a basic understanding of the ability of transformed *Staphylococcus epidermidis* (SE) to compete against wild type SE. In order to understand the growth characteristics of the transformed bacteria and the growth dynamics of recombinant, protein-producing bacteria, standard methods of growth in liquid media were used. In order to determine growth differences between SE-sGFP, SE-chl (empty vector control, resistant to chloramphenicol (chl)), and wild type SE, each strain was grown separately in 100 mL cultures each for 6 hours. Every 45 minutes (the approximate doubling time of SE), 1 mL samples were taken and measured at 600 nm to obtain measurements of the total concentration of bacteria. Optical density was compared across all samples to understand growth characteristics.

Results are shown in FIG. 1. As shown in FIG. 1, protein production only slightly diminished the competitive growth of SE-GFP relative to SE as determined by CFU measurements. It is expected that diminished growth is due to the increased metabolic demand in protein-producing SE.

Example 2. Quantification of Growth of SE-GFP and Control Strains on Reconstituted Human Epidermis (RHE)

In order to characterize the feasibility of applying bacteria to the skin, the growth dynamics of externally applied bacteria on an in vitro skin model were determined. This model provided an initial approximation of the ecological competition these bacteria would encounter on human skin. RHE cultures were established and maintained in antibiotic- and antifungal-free media (supplemented with chloramphenicol as needed). SE-sGFP suspended in 50% glycerol were applied with a pipette to the center 3 mm diameter of the RHE. Control RHE with SE-chl and SE-WT bacteria were also applied alongside the experimental arms. At pre-determined timepoints, the tissue inserts removed, homogenized and passed through a 40 μm filter to allow for collection of bacterial flow through. The bacterial suspension was spun down, resuspended in media, serially diluted and plated to determine the CFUs of bacteria. All measurements were normalized to the maximum recovery of bacteria as determined by the CFUs present 15 minutes after application.

Results are shown in FIG. 2. As shown in FIG. 2, SE-GFP grew more slowly than SE with an empty vector when applied on RHE separately. While growth of control SE plateaus by 24 hours, SE-GFP bacteria plateau by 48 hours and the final counts are ~½ log lower. When added together to simulate the competition on human skin, SE with the vector alone outgrew and slightly outcompeted the protein-producing SE with at least one log difference of CFU (FIG. 2). These results, combined with those above, led to the conclusion that protein-producing SE may have a slight disadvantage when colonizing the skin in a clinical setting, potentially requiring additional genetic modification to facilitate growth and competition. However, as shown in Example 3, these bacteria are well able to colonize skin models.

Example 3. Qualitative Characterization of Growth of SE-GFP and Control Strains on RHE The purpose of this experiment was to add spatial and temporal information about SE-GFP colonization using RHE and the Vivascope. SE-GFP was applied to RHE for 3.5 hours, and samples were imaged in reflectance and fluorescence modes in three standardized regions of 2 mm×2 mm wide and 100 μm deep using 4.75 μm steps and linear increase in laser power. Ultrasound gel (Parker Laboratories) was used to preserve the refractive index between the objective and the glass sample plate. Importantly, in order to mimic the hyperstructure of damaged skin in AD patients, the RHE was intentionally punctured with a Derma Microneedle device to determine the localization of the bacteria in the presence of damaged skin. The results showed that the bacteria, applied at $10^8$ CFUs and grown at 3.5 hours, localized to the puncture at depths up to 70 μm (arrows, FIG. 3B and FIG. 3C). This suggests that topically applied bacteria will be able to hone to areas of damaged skin.

The results from these experiments showed that the modified bacteria hone to the surface and deep grooves of the stratum corneum layer and maintain a constant presence over the course of the experiment. These experiments also showed that SE hone to skin barrier defects and this suggests that our bacteria would colonize more deeply in skin that is impaired, as we expect in AD patients (FIG. 3A-C).

Figure 4A:
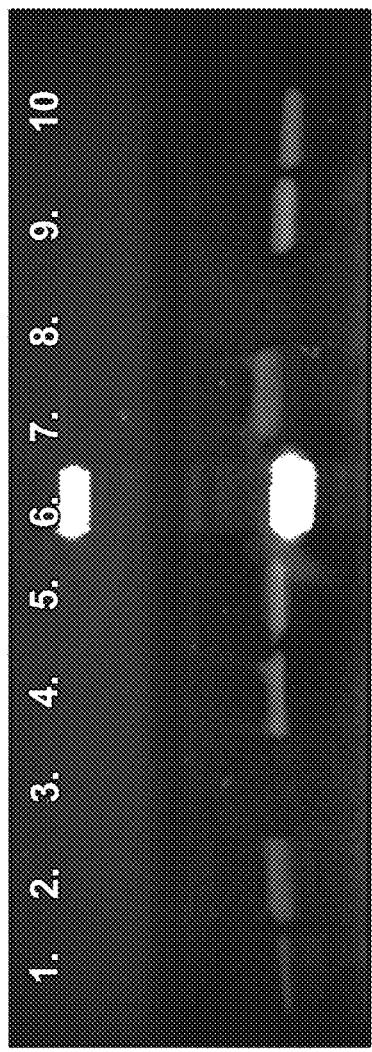
Figure 4B:
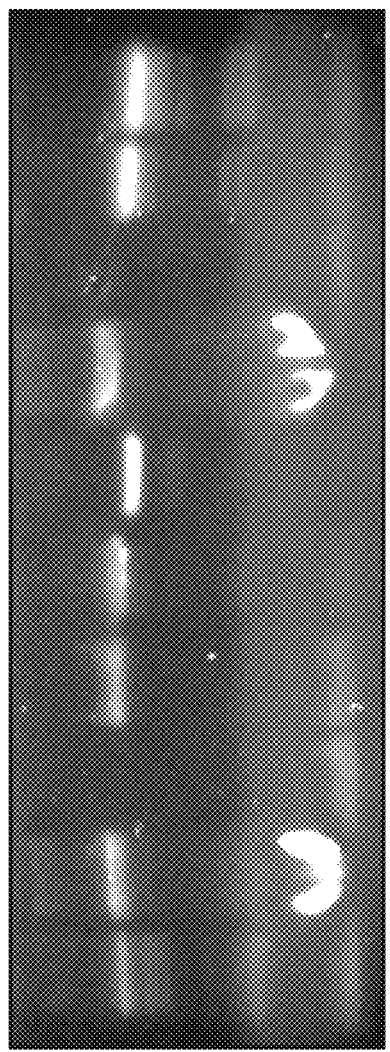
FIG. 4B and FIG. 4C show fluorescence and light wavelength overlays of RHE 3.5 hours at 37° C. after Dermaroller application followed by topical GFP application, showing the bacteria have localized into the breach of a damaged stratum corneum with no evidence of bacteria in epidermis at that level. Depths taken at 50 μm FIG. 3B and 70 μm FIG. 3C.
Figure 4C:

Example 4. Characterization of Delivery of Bacterially Secreted sGFP to the Skin Using an In Vitro Model System Isolation of sGFP produced by SE Protein was purified from 225 mL culture of SE (2.7-2.9 OD/mL and lysed with CellB-Lyse (Sigma). 4 mL eluate was produced and ran with 500 mM imidazole from a Ni-NTA column in a BPS buffer at pH 7.4 and yielded 0.4 mg per 225 mL of SE. SDS-PAGE gels of purified sGFP are shown in FIG. 4.

Characterize Delivery of Bulk Purified sGFP and sGFP+ RMR to RHE and Characterize Cellular Compartment and Depth of Penetration sGFP Protein from SE-GFP Reporter and Control Strains.

The localization of purified sGFP and sGFP+RMR was examined to answer three important questions: (1) does sGFP+RMR penetrate the stratum corneum; (2) if so, how deeply can it be detected; and; (3) what are the kinetics of penetration. 5.0 μg of GFP+/−RMR was applied to RHE. Two-photon microscopy and confocal imaging were used to examiner the effects at 30 minutes and 60 minutes to examine penetration and kinetic. Importantly, both intracellular localization of GFP due to the effects of RMR to penetrate human cells was examined, as well as the transdermal localization of GFP due to the effects of RMR in facilitating dermal penetration.

Figure 5A:
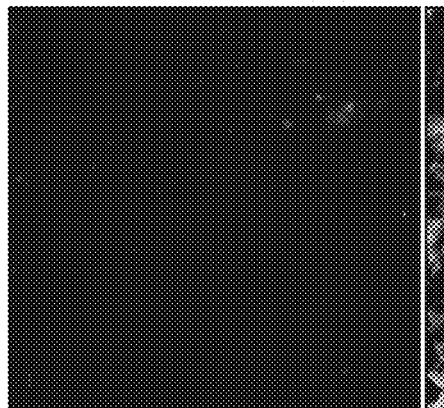
Figure 5B:
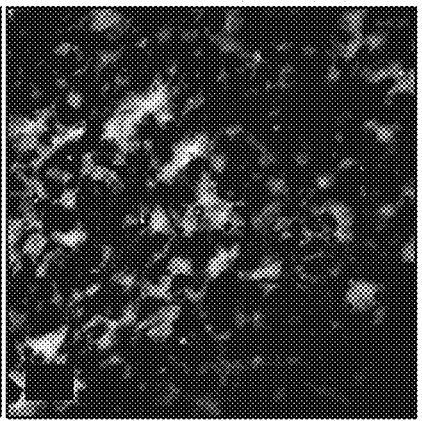
Figure 5C:
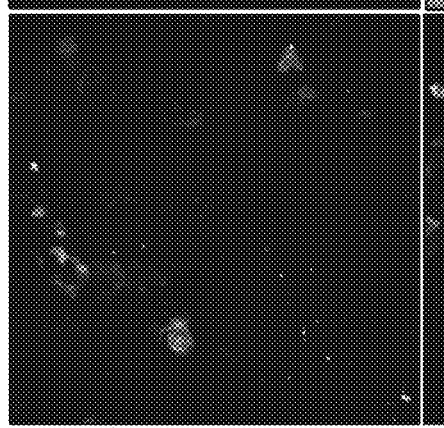
Figure 5D:
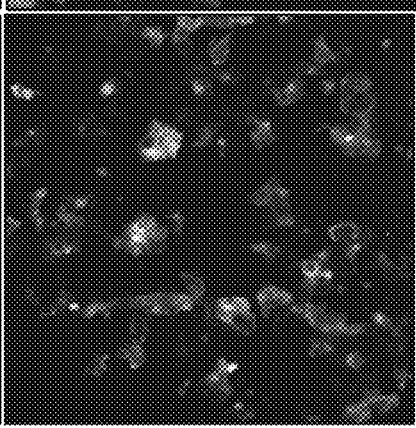
Figure 5E:
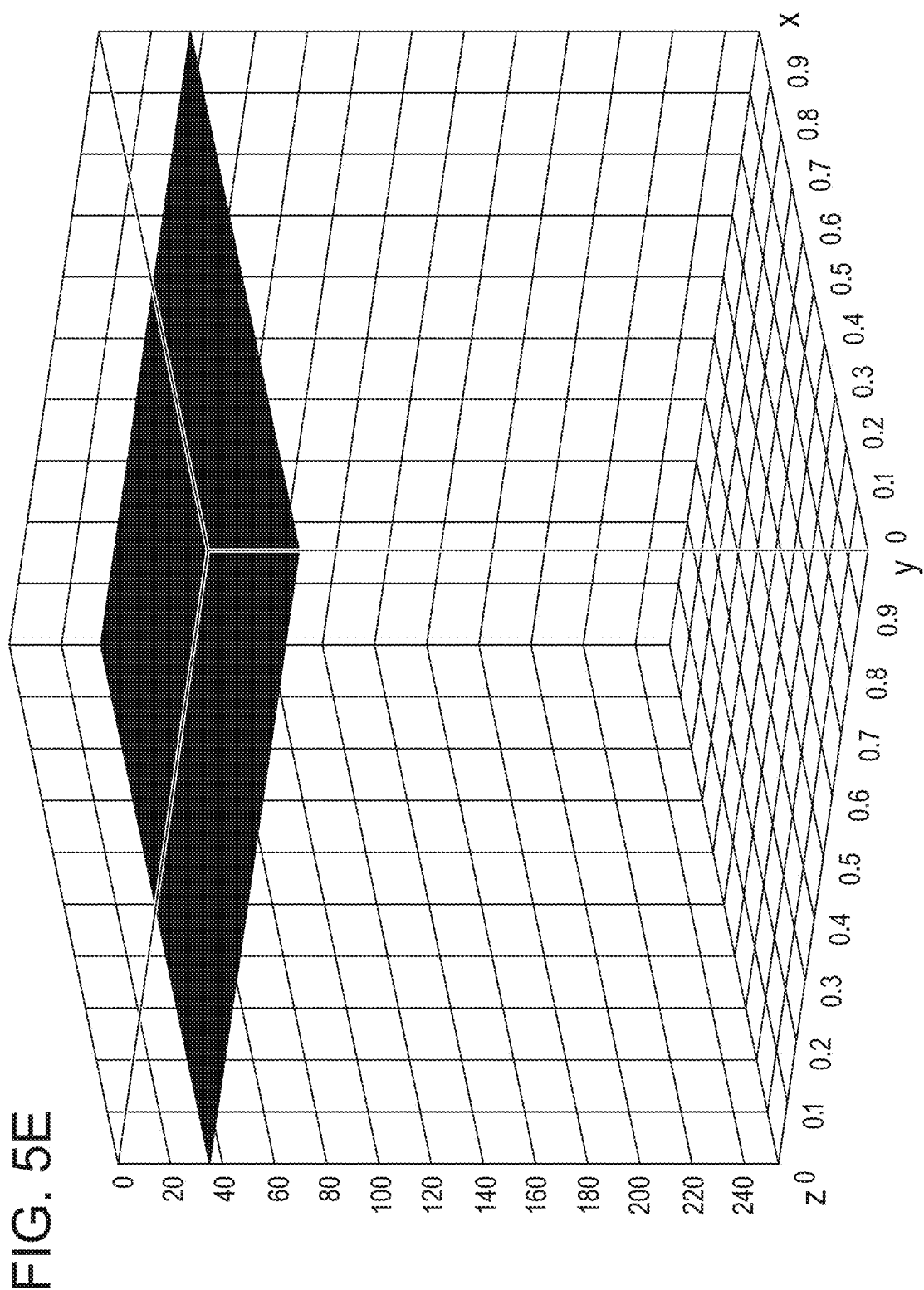
(FIG. 5E-FIG. 5H) 3D surface analysis to examine depths of protein penetration into RHE (FIG. 5I-FIG. 5N) Confocal images of GFP (K, N) GFP+RMR (FIG. 5J, FIG. 5M) or vehicle (FIG. 5I, FIG. 5L) using light (FIG. 5L-FIG. 5N) or fluorescent (FIG. 5I-FIG. 5K) wavelengths.
Figure 5F:
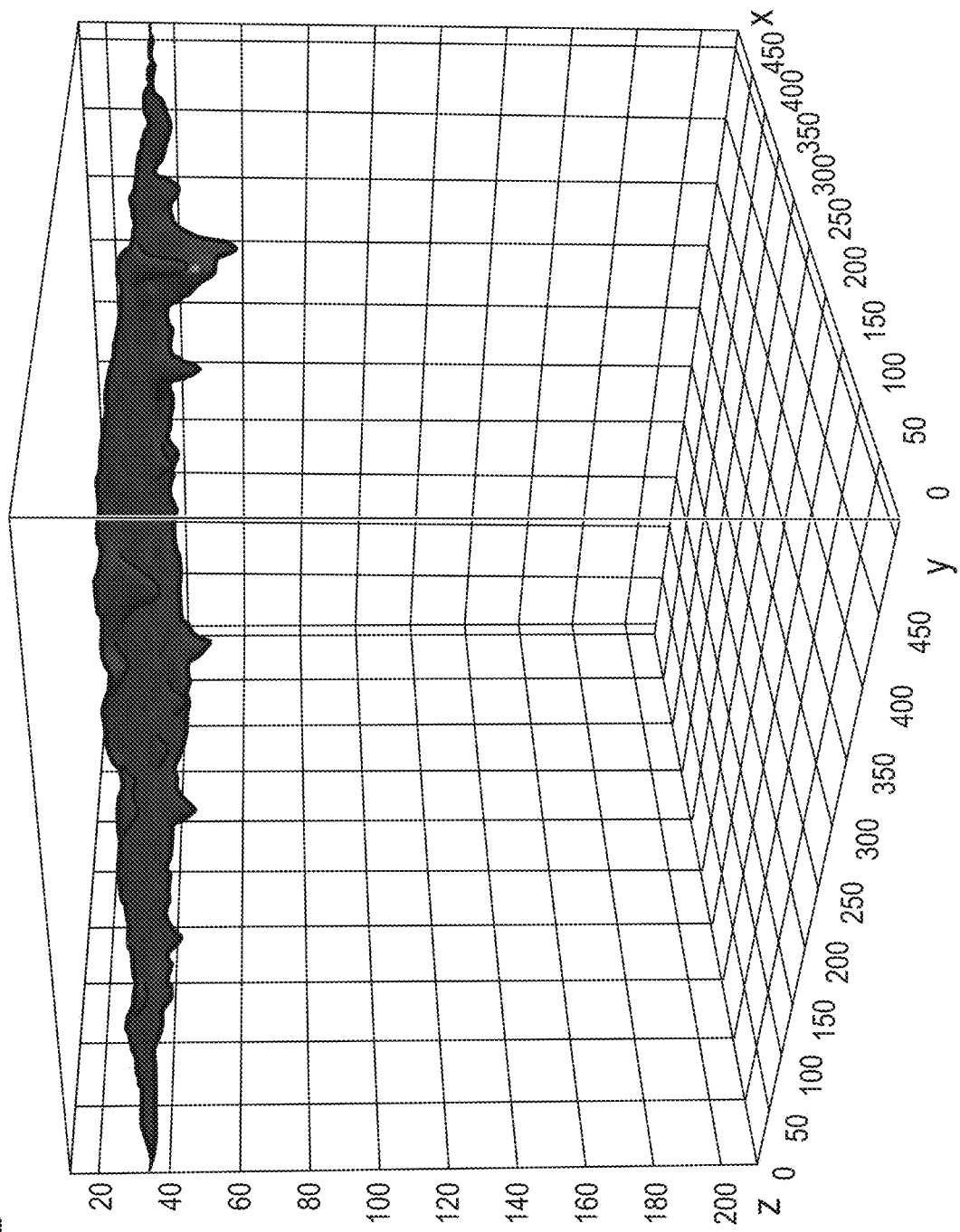
Figure 5G:
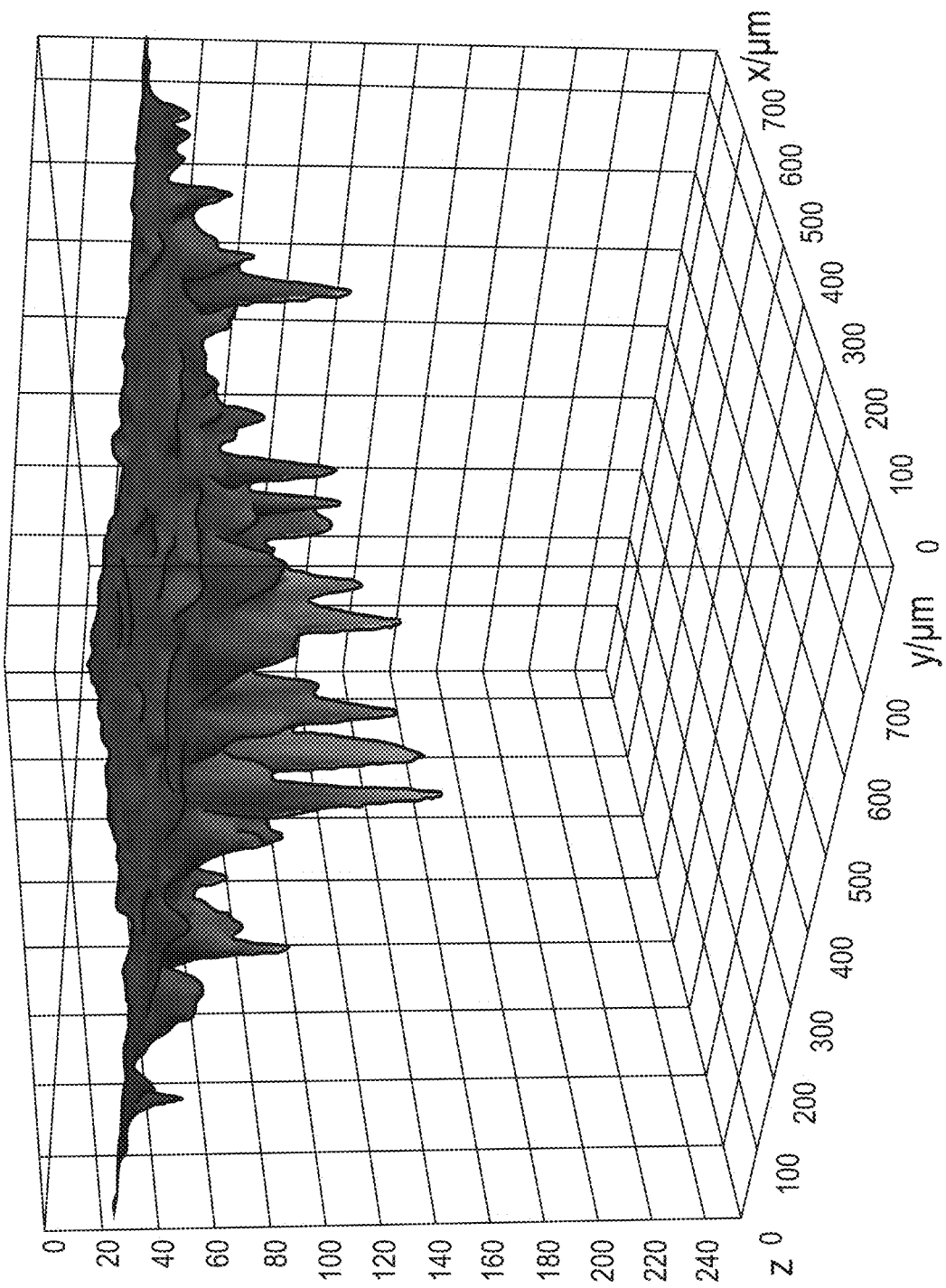
Figure 5H:
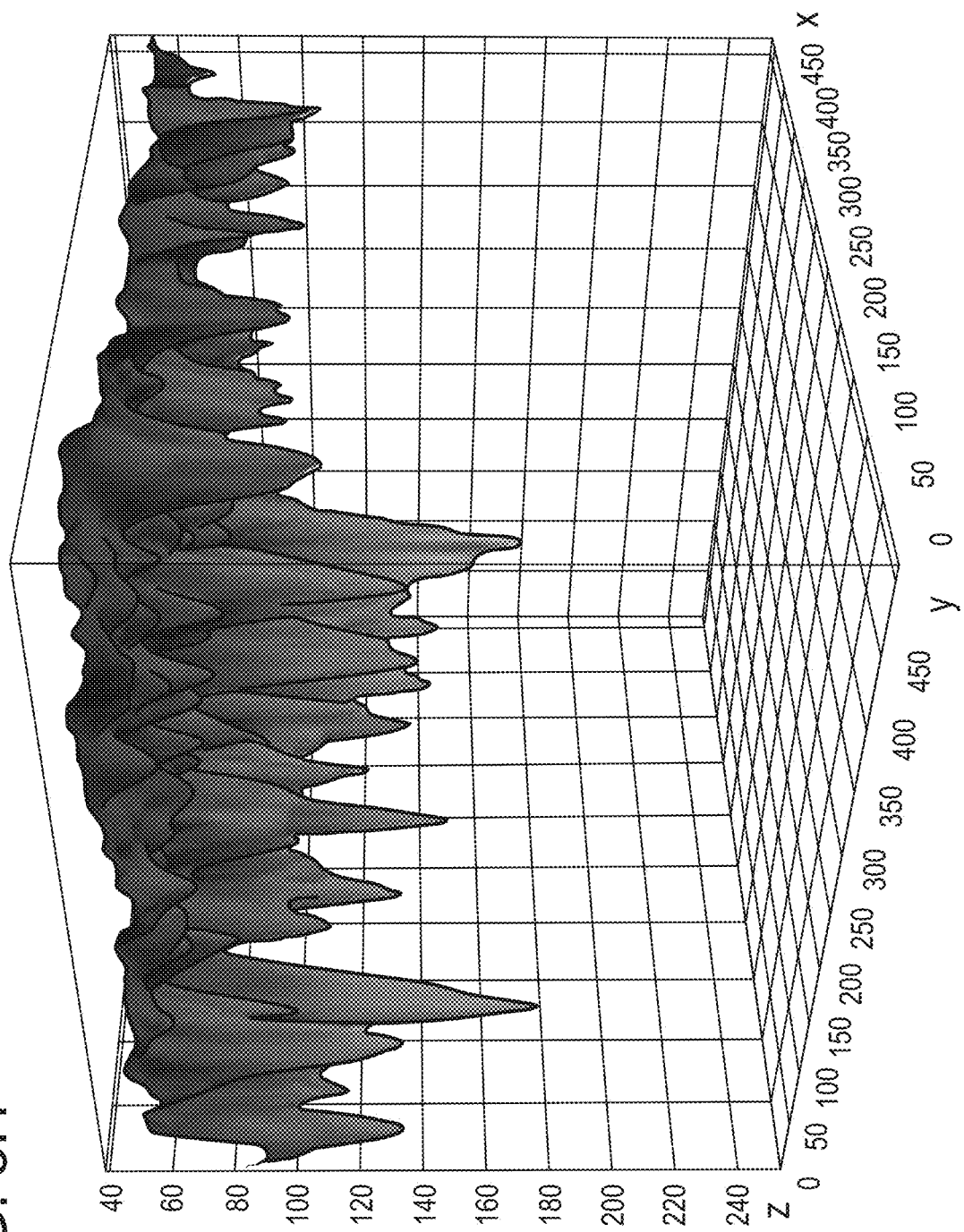
Figure 8:
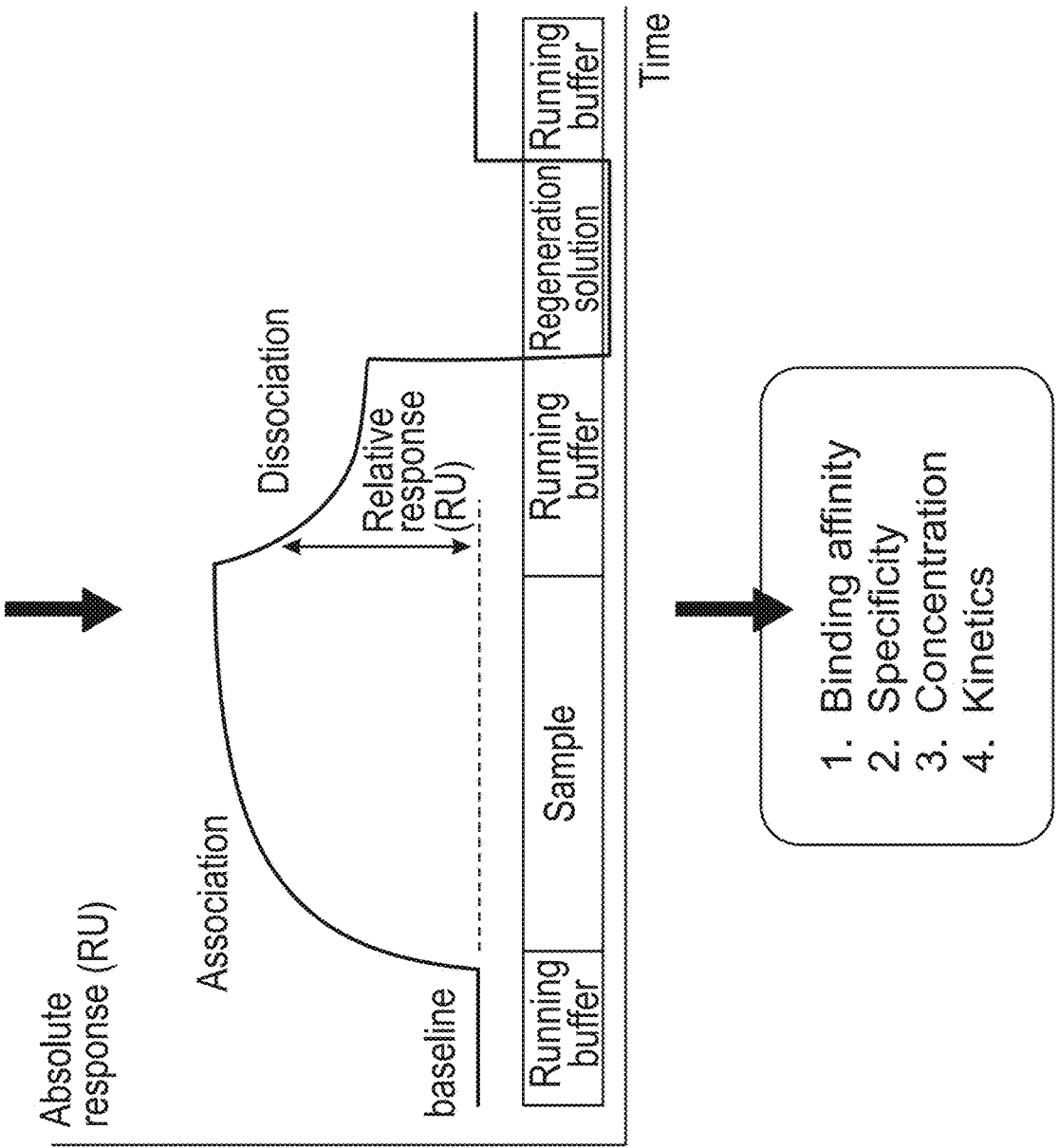
FIG. 8 shows overview of Biacore surface plasmon resonance (SPR) for filaggrin activity.

The results of these experiments showed that GFP without the RMR did not effectively penetrate RHE (FIG. 5A, B, E, F). However, the same amount of GFP-RMR was more deeply delivered into the tissue (FIG. 5G, H, J) compared to GFP without the RMR signal (FIG. 5E, F, K), supporting the efficacy and necessity of the RMR for transdermal penetration. Additionally, evidence of GFP with the RMR accumulating in keratinocytes was found (FIG. 5C, D), compared to GFP without the tag (FIG. 5 A, B), supporting intracellular penetration. Overall, these results indicate that the RMR facilitate transdermal delivery of our protein, which is highly relevant for delivering filaggrin more deeply into the skin of IV patients with treatment with filaggrin-producing SE. Depth and localization of GFP following breaching the stratum corneum with the Dermaroller was examined, and it was found that the GFP preferentially localized and penetrated into the breached area (FIG. 5O).

Example 5. Analytical Method Development and Optimization of Human Filaggrin Production from *Staphylococcus epidermidis*

Analytical methods for filaggrin quantification were developed, as well as a structure-activity approach to rationally select the optimal filaggrin oligomer and sequence to move forward in preclinical and subsequently clinical development.

Rational Design of Filaggrin Sequence

A filaggrin molecule that was based on what is thought to be a domain containing sequences flanked by proposed linker regions at both ends was used as the starting point. hFLG is comprised of 12 repeating units and is processed by intracellular proteases to release the individual units. An overview of filaggrin structure is presented in FIG. 6E. See FIG. 6A, B for bioinformatics analyses studying the homology and sequence identify of the human filaggrin domains. The sequences within these units are highly homologous. It has been proposed that the units are cleaved at “linker regions.” The segments between these linker regions are the individual units, with each unit containing a pair of sub-domains. The spatial orientation or topography of these units has not been resolved because the molecules are not highly structurally organized. Based on Kyte-Doolittle hydropathy scoring, the linker regions were defined as the most lipophilic amino acid segments in the hFLG protein (FIG. 6C, D).

In an effort to study the SAR of hFLG, the entire unit containing sub-domains 9 and 10 flanked by their linker regions were recombinantly produced. To identify the minimum protein segment responsible for keratin binding activity, therefore, proteins were produced with systematically shaved off regions of the N-terminus. The role of the linker region is also examined. To address this question, proteins are being prepared where the linker region is centered within the sequence. An RMR peptide sequence is shown in FIG. 6E, FIG. 6E based on the previous characterization of the delivery of GFP via an RMR (FIG. 5A-N). As described below, a structure-activity relationship (SAR)-based approach to select the optimal filaggrin sequence of the possible sequences that have been identified is used.

Example 6. Identification and Quantification of Filaggrin Secreted by SE

Critical to later preclinical and clinical development of a filaggrin-secreting SE strain, methods to identify and quantify filaggrin secreted by SE were developed.

Antibody Development and Immunoreactive Detection of hFLG

An antibody (RL-012-001B, a chicken IgY), was developed against an epitope of hFLG that is common across all pairs of sub-domains. This was necessary because commercially available filaggrin antibodies displayed significant non-specific binding. This IgY antibody demonstrates a clean band on Western blots for filaggrin isolated from cells lysate of filaggrin-producing SE and its media (FIG. 7D). The IgY was able to recognize several different pairs of hFLG subunits that were produced (FIG. 7 B-D).

Mass Spectrometry (MS)

Preliminary LC-DDA-(Data Dependent Acquisition) MS/MS analysis of 20 ng of human filaggrin segments 9-10 are presented in FIG. 7E. This identifies peptide sequences that can be followed as filaggrin production, secretion and delivery is monitored.

The protein sample is re-suspended in 50 mM ammonium bicarbonate buffer and digested with trypsin by incubating overnight at 37° C. The sample is then acidified to halt the trypsin activity, and then desalted using C18 spin columns, the eluates of which are then dried under vacuum-centrifugation and re-suspended in 0.1% formic acid. The resulting trypsin digest is analyzed by reverse-phase LC-DDA-MS/MS using nanoACQUITY UPLC system connected to an Orbitrap-Fusion Tribrid mass spectrometer equipped with a nanoelectrospray source. After injection, the peptides are loaded into a trapping column and then separated with a C18 column.

LC-DDA-MS/MS analysis is performed at with the mass spectrometer operating in a Top Speed data-dependent mode with maximum total cycle time of 3 sec. During MS1 full scan, precursor ions are isolated in the quadrupole mass analyzer, recorded with a maximum injection time of 60 ms, an automatic gain control (AGC) target value of $4\times10^5$, and an Orbitrap resolution of 120,000 at m/z 200. A full scan is acquired in the range of 300-1500 m/z, followed by MS2 of the most intense ions. The ions are iteratively isolated with a 1.6 Th window, injected with a maximum injection time of 110 ms, AGC target of $1\times10^5$, and then fragmented with higher-energy collisional dissociation (HCD) of 28. The MS/MS spectra are then recorded at a resolution of 60,000 at m/z 200. Ions with single charge or unassigned charge states are excluded from fragmentation.

The reliability and robustness of this assay are critically important for biochemistry, manufacturing, and controls of any eventual LBP comprised of filaggrin-secreting SE. Qualification of the MS analytical methods uses the following metrics: (1) specificity; (2) sensitivity (Limit of Detection (LOD) and Limit of Quantitation (LOQ); and (3) Linearity. This will be accomplished using reference standards of purified hFLG and running multiple samples over a range of concentrations. As illustrated in FIG. 7E, specific peptides are detectable, and several of these can be prepared synthetically as reference standards, if necessary.

Example 7. Keratin Binding Assay to Measure Activity of Filaggrin

A keratin binding assay is used to measure activity of filaggrin. This will be assessed by surface plasmon resonance (SPR) method (Biacore GE Healthcare) to rank different filaggrin segment based on their cytokeratin interaction. This will measure the binding affinity, specificity, concentration, and kinetics to examine filaggrin-cytokeratin binding dynamics. Expected metrics produced by this method include $K_{on}$, $K_{off}$ and $K_d$. Different human cytokeratins will be evaluated starting with cytokeratin 1 and 10, known to interact with hFLG. The assay will be developed with our current filaggrin 9-10 construct and will be used to measure addition filaggrin sequences to guide the SAR analysis. The assay workflow is presented in FIG. 8.

Example 8. Optimization of Human Filaggrin Through Structure-Activity Relationship (SAR)

Based on the methods described above and shown in FIG. 6, the remaining 11 filaggrin domains will be tested and a matrix of identity and activity will be generated, as outlined by the above methods (i.e. Western blots, MS, and surface plasmon resonance (SPR) protein-protein interaction assays). The correlation of protein sequence and in vitro activity will guide the selection of the protein to be produced as a potential therapeutic agent.

Example 9. Conduct Analytical Method Development and Optimization of Human Filaggrin Delivery from Staphylococcus epidermidis to a Human Skin Model Critical to the characterization of later pharmacokinetics (PK), assays will be developed for detection and distribution of filaggrin. This will include characterization of filaggrin distribution in human skin models (reconstructed human epidermidis) as well as mouse skin from filaggrin-producing SE using MS (as described above) to detect intact and breakdown products, as well as immunofluorescence and immunohistochemistry. The measurement of filaggrin breakdown products will also supplement the characterization of activity of filaggrin, i.e. internationalization and processing of filaggrin. Additionally, assays will be developed to detect filaggrin breakdown products, including Raman spectroscopy.

Flg-/- Reconstructed Human Epidermis (RHE)

Filaggrin KO reconstructed human epidermis, branded as EpiDerm, will be purchased from MatTek (Ashland, MA). The Epiderm model is constructed from normal human epidermal keratinocytes (NHEK) from neonatal foreskin or adult breast skin of a single donor. The model is supplied as 9 mm diameter tissue samples that have been grown on Millicell CM (Millipore) exposed to an air-liquid interface. Epiderm recapitulates eight to twelve layers total of basal, spinous, and granular differentiation and ten to fifteen layers of stratum corneum. Histologically, metabolically, and genetically, Epiderm provides excellent correspondence to human skin. Models maintain morphology for up to three weeks. Filaggrin knockdown in keratinocytes will be achieved via shRNA lentiviral-based knockdown of filaggrin. An estimated 96 RHE samples will be needed for this aim.

Mouse Models

Both wild type BALB/c and flg-/- mice will be used. BALB/c mice will be purchased from Jackson Laboratory, Bar Harbor, ME, and flg-/- have been obtained by Azitra from Riken Laboratory (Nagaski, Japan). An estimated 22 BALB/c and 22flg-/- will be needed for this aim.

Immunofluorescence and Immunohistochemistry

To understand and characterize the absorption and biodistribution of filaggrin secreted by the SE, immunofluorescence (IF) microscopy and immunohistochemistry (IHC) will be used to visualize filaggrin localization and distribution from filaggrin-producing SE. To do this, flg-/- reconstructed human epidermis (RHE) will be used. Briefly, a range of $10^6$ to $10^8$ colony forming units (CFUs) of filaggrin-producing SE will be applied to the RHE and mouse skin and incubated for 24 hours without antibiotics. Samples will be fixed for IF and IHC analyses at 24, 48, and 72 hours in triplicates and untreated RHE and mouse samples will serve as negative controls for these analyses.

For IF, samples will be fixed with 70% ethanol, 50 mM glycine for 1 hour. Immunofluorescence staining will be performed by incubation of our developed anti-filaggrin primary antibody (RL-012-001B) at 1:200 for 2 hours, followed by incubation with rat anti-goat rhodamine secondary antibody (Jackson Laboratory) at 1:200 dilutions in the presence of Hoechst Stain Solution (Sigma). Slides will be mounted with coverslips in Gel/Mount (Biomed).

For IHC, samples will be fixed in 10% formalin and paraffin embedded. Paraffin sections will be dewaxed and washed with 95% ethanol followed by methanol hydrogen peroxide. The sections will then be treated with a heat induced epitope retrieval (HIER) procedure using rodent Decloaker solution (Biocare Medical, RD913) and the Biocare decloaking chamber. After being washed in Tris pH 7.4, sections will be incubated in the presence of rat serum and FcBlock (24G2) followed by rabbit anti-S. epidermidis diluted in the blocking solution. Samples will be washed in Tris and then incubated with goat anti-rabbit IgG-Texas Red antibody (Invitrogen, T2767). The tissue will then be counterstained with HOECSHT and imaged using a Leica DM IRBE fluorescent microscope.

Raman Spectroscopy

Raman spectroscopy is a known method to identify NMF breakdown products of filaggrin.[62] During terminal differentiation, pro-filaggrin is rapidly dephosphorylated and cleaved to yield functional filaggrin monomers, which bind to and assemble keratin intermediate filaments.[63,64] Cleavage of deiminated filaggrin monomers is catalyzed by several proteases, including caspase 14,[65] calpain 1, and bleomycin hydrolase.[66] Filaggrin is then broken into natural moisturizing factors (NMFs), specifically urocanic acid (UA) pyroglutamic acid (PGA) and citrulline (CiT).[62]

Raman spectroscopy will be used to identify filaggrin breakdown products in flg-/- RHE models and mouse skin. The Raman effect consists of a shift in photon energy due to inelastic collisions of photons with molecules. The Raman spectrum shows the scattering intensity as a function of the frequency difference between the incident and the scattered light; this difference is known as the "Raman shift." An initial Raman spectroscopy method has been developed to identify the breakdown products of filaggrin, NMFs. The skin (RHE) can be observed directly without sample preparation of destruction of the tissue. At this time, samples of commercial standards have been used to test the method, and the results of this are presented in FIG. 9A-D.

Raman spectroscopy is capable of detecting micro-molar concentrations when optimized. Nano-molar detection levels are possible using surface-enhanced Raman spectroscopy, in which nanoparticles of a suitable material (either gold or silver) can be placed on the skin sample. These particles undergo surface plasmon resonance, thus significantly increasing the sensitivity of the Raman analysis. This will be used to identify filaggrin breakdown from filaggrin-producing SE applied topically to RHE. $10^8$ colony forming units (CFUs) of filaggrin-producing SE will be applied to the RHE and incubated for 24 hours without antibiotics. Samples will be collected and analyzed at various timepoints using Raman spectroscopy to identify NMF breakdown products.

Mass Spectrometry

Figure 9B:
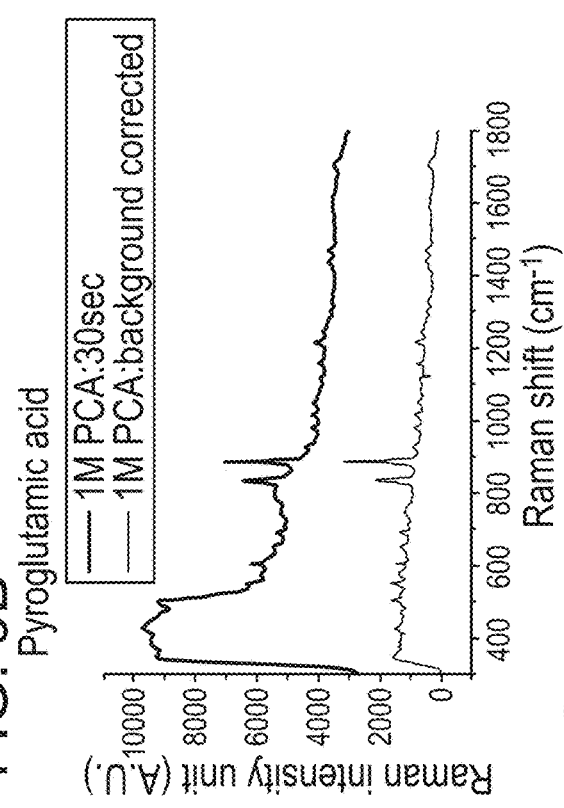
FIG. 9A-FIG. 9G shows pilot results of creating standard curves for filaggrin breakdown products, or natural moisturizing factors (NMFs). Raman spectroscopy can detect individual NMF components (FIG. 9A-FIG. 9D). Mass spectroscopy (FIG. 9E-FIG. 9G) is also very sensitive with limit of quantitation (LOQ) in the pictogram to nanogram range.
Figure 9D:
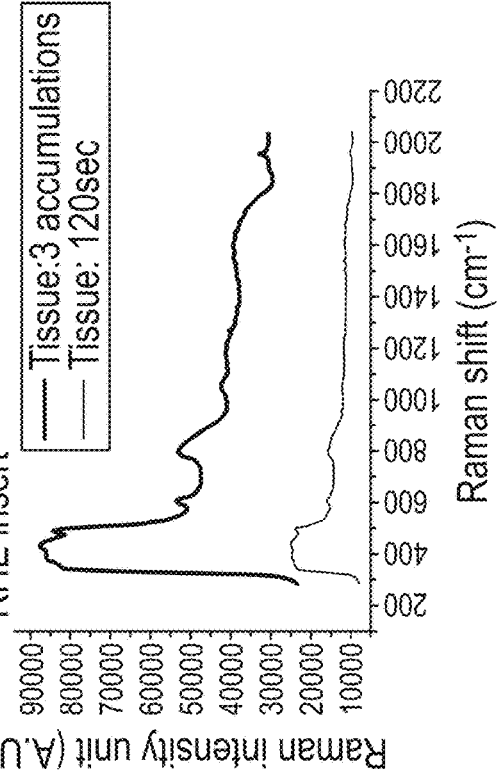
Figure 9A:
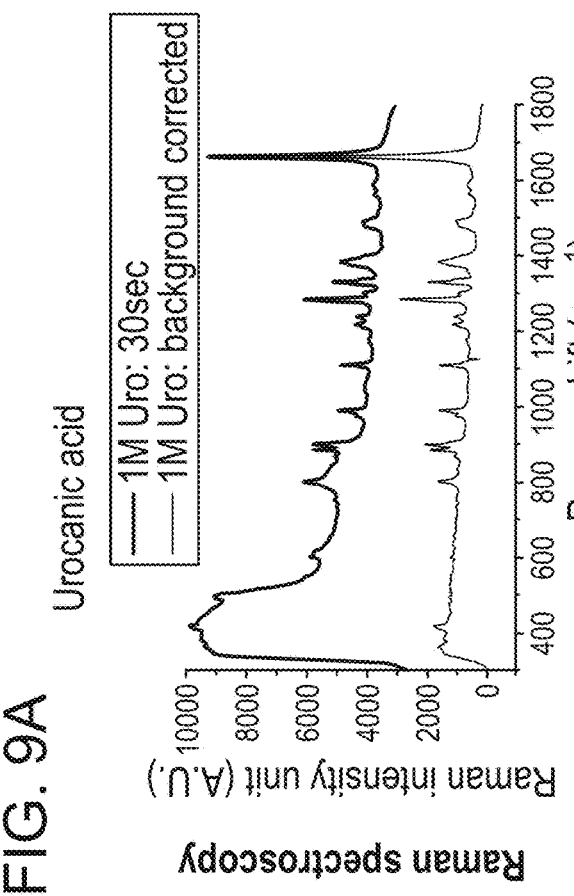
Figure 9C:
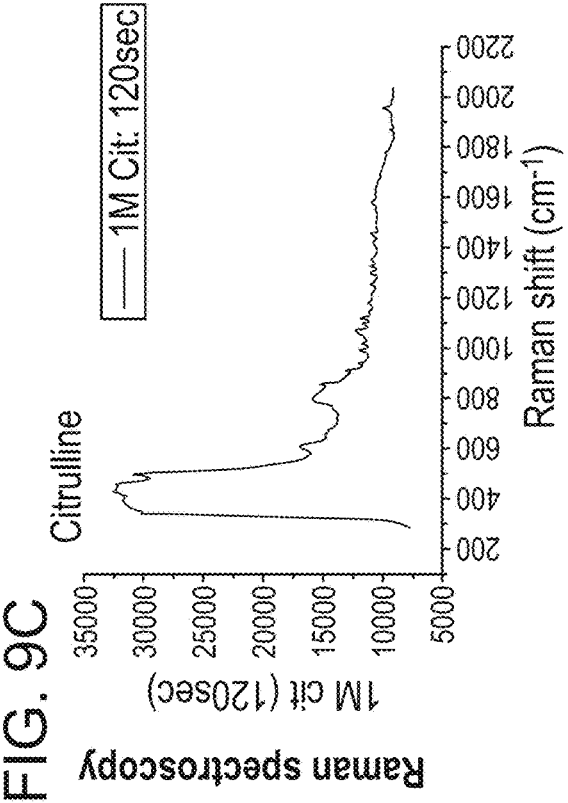
Figure 9G:
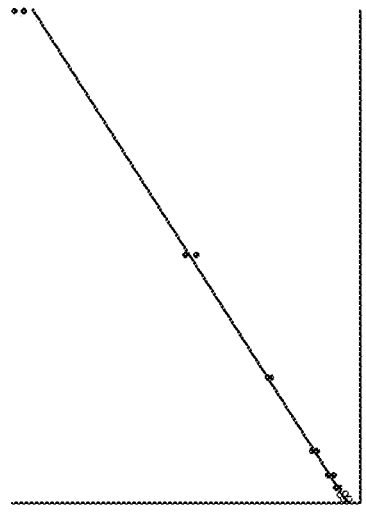
Figure 9F:
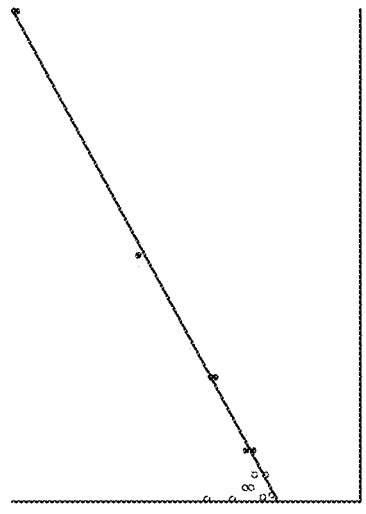
Figure 9E:
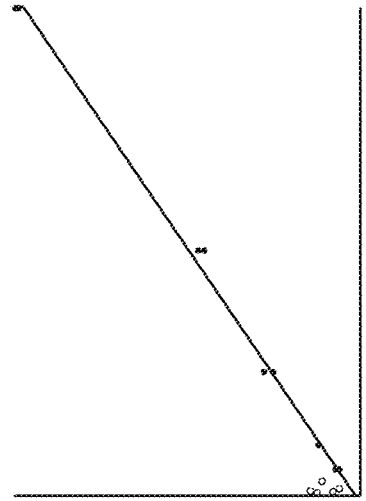

To estimate and characterize metabolism of filaggrin, mass spectrometry will be used. Detection of commercial standards of the NMF molecules, urocanic acid (UA) pyroglutamic acid (PGA) and citrulline (CIT), has been be performed using an Agilent HP1200 mass spectrometer coupled with AB Sciex API4000 QTrap. Standards of UA, PGA and CIT were purchased from Sigma-Aldrich and were separated with Agilent Eclipse XDB C18 column (3.5 u, 2.1×100 mm) injected into the spectrometer and detected by MRM (multiple reaction monitor) and Secondary-ion mass spectrometry (SIMS). SIMS appeared to be about ten times more sensitive than MRM. The Limit of Quantization (LOQ) for UA, PCA and CIT are 0.5, 1, and 0.25 ng/mL respectively, and standard curves showed correlation coefficients of 0.99. When testing for the production of NMFs from FLG in RHE experiments, the RHE tissue samples will be homogenized and extracted with perchloric acid/acetonitrile, and the resulting solution injected. Standard curves of these results are presented in FIG. 9E-G. These preliminary data suggest that CIT will probably only be detected using MS rather than Raman spectroscopy.

These parameters will be used to measure filaggrin breakdown from filaggrin-producing SE applied topically to RHE. $10^8$ CFUs of filaggrin-producing SE will be applied to the RHE and incubated for 24 hours without antibiotics. Samples will be collected and analyzed at various timepoints using MS to detect NMF breakdown products. This assay will also be qualified using (1) specificity and sensitivity; (2) accuracy and precision; (3) limits of the assay using the methods described above. The results of this will inform initial metabolism and distribution of filaggrin in two models.

Example 10. Evaluate Colonization Dynamics and Activity of Candidate Filaggrin-Secreting SE in Mice A genetic IV mouse model (Flg−/−) will be used, as well as wild type mice to assess colonization dynamics of FLG-producing SE in vivo.

Mouse Models

In order to investigate the applicability of this approach, a genetic model mouse system will be used. The filaggrin knockout mouse (Flg−/−). Flg−/− mice are filaggrin deficient and exhibit dry, scaly skin.[19] Despite marked decreases in natural moisturizing factor levels, which are filaggrin degradation products, stratum corneum (SC) hydration and TEWL are normal in Flg−/− mice. Antigens penetrate the Flg−/− SC more efficiently, leading to enhanced responses in hapten-induced contact hypersensitivity and higher serum levels of anti-ovalbumin (OVA) IgG(1) and IgE. Flg−/− mice are obtained from RIKEN BioResource Research Center (RIKEN BRC, Tsukuba, Ibaraki, Japan) via a material transfer agreement. Wild type mice (BALB/c) will also be used in this experiment.

Study Design

Figure 6A:
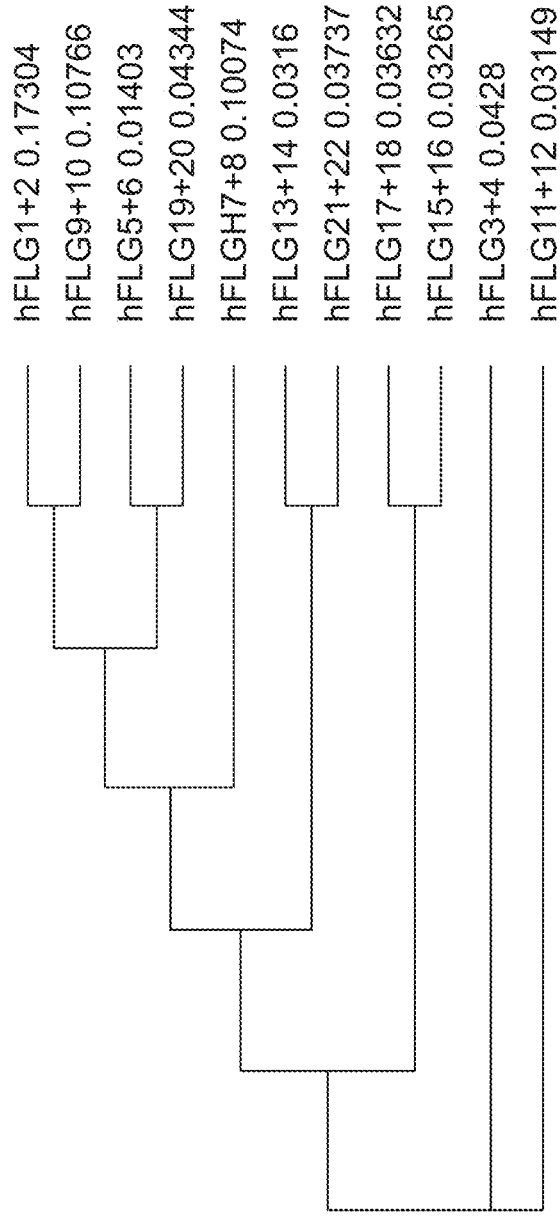
Figure 6B:
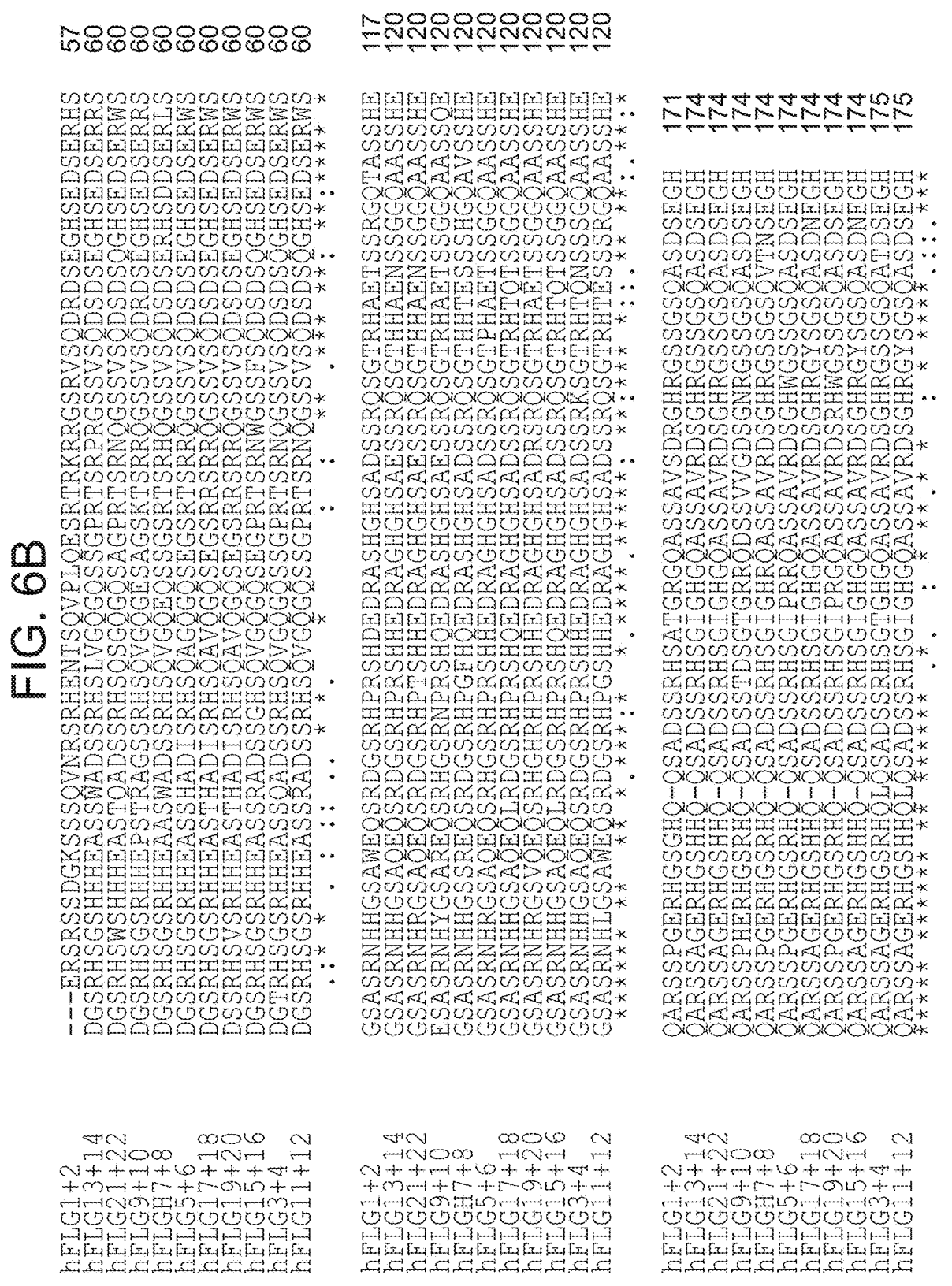
Figure 6C:
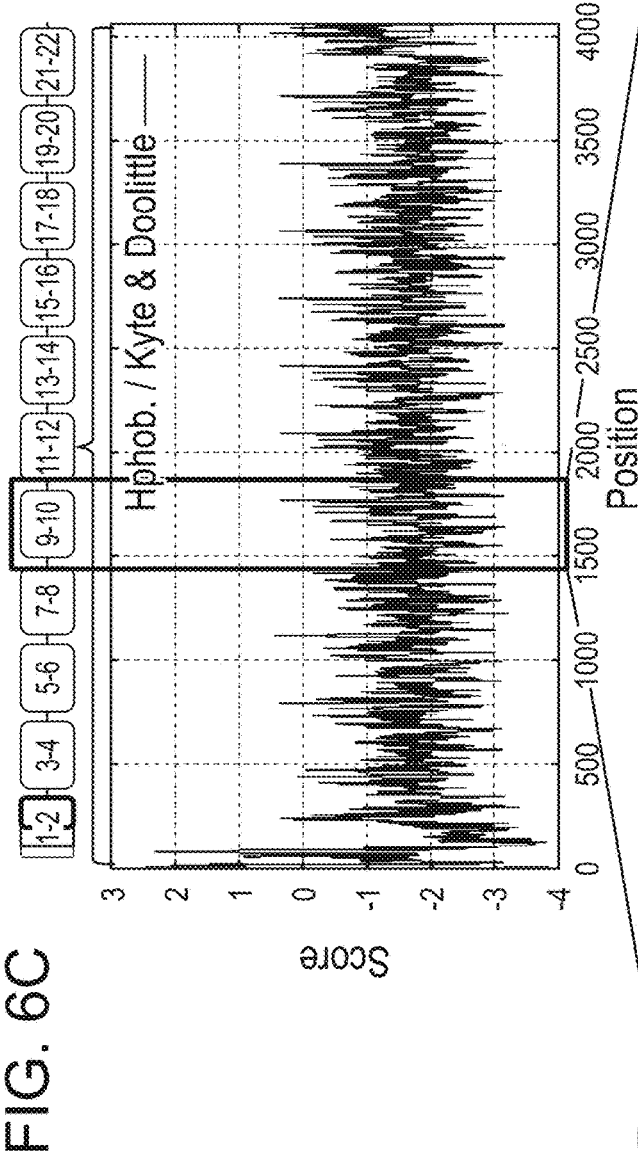
Figure 6D:
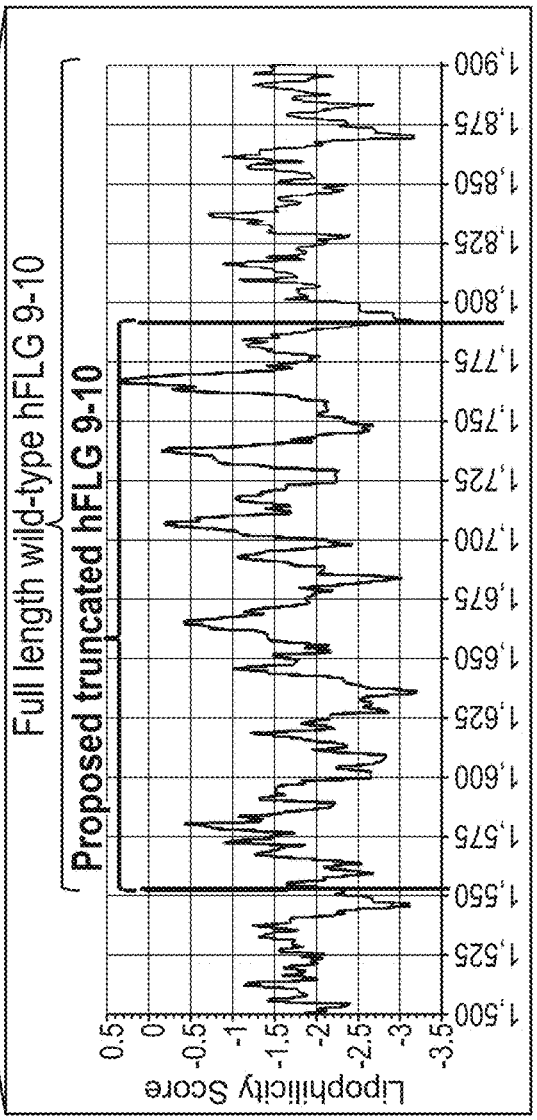
Figure 6F:
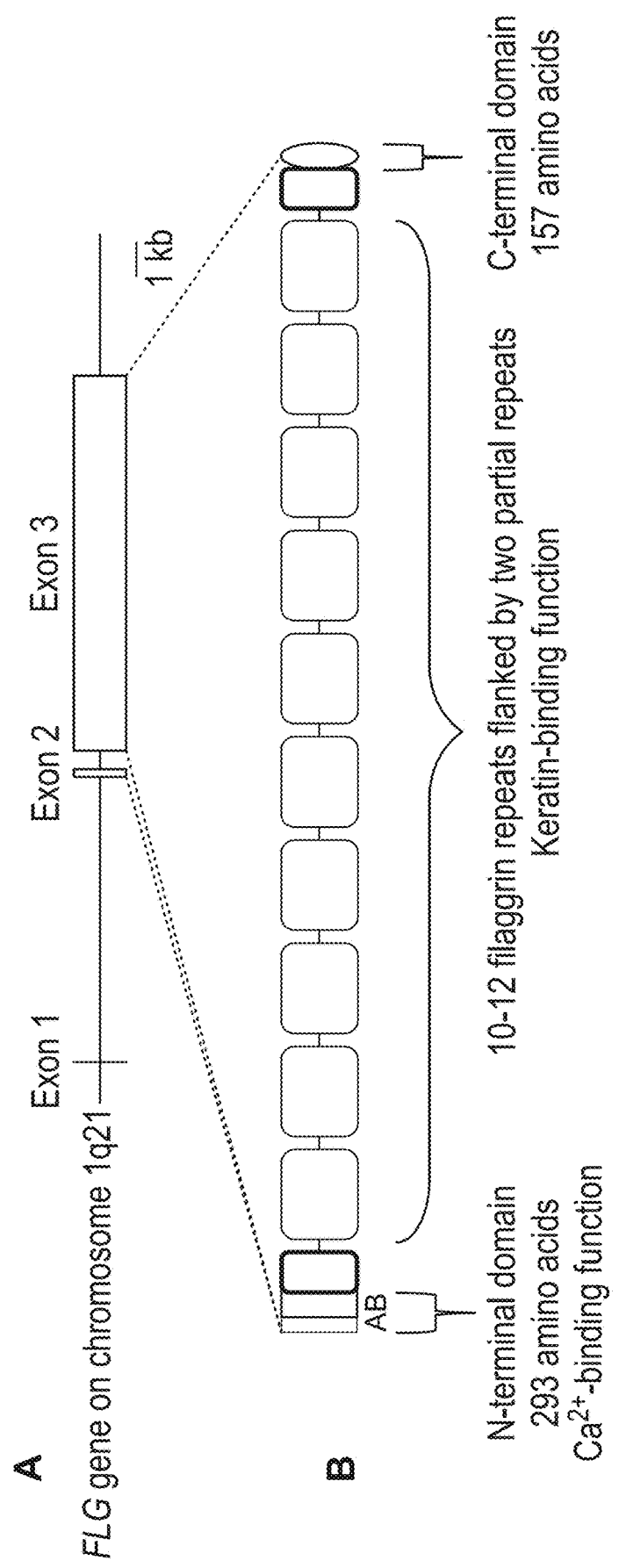
Figure 10:
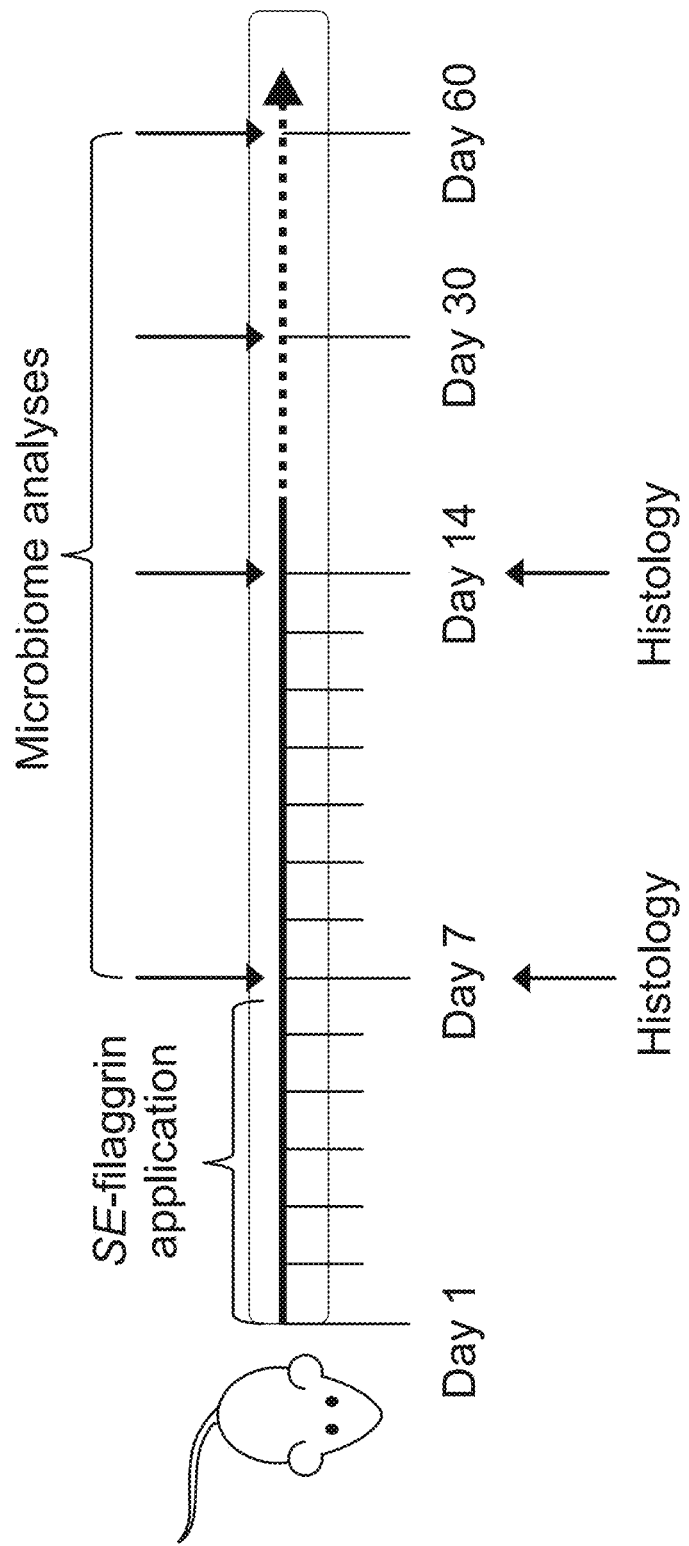
FIG. 10 shows overview of workflow.

The designed filaggrin sequence from FIG. 6E will be used in SE to Flg−/− and BALB/c mice. The study will be conducted for four weeks using five groups in each mouse type. Mice will be assigned into the following treatment groups: topical vehicle control (50% glycerol, 50% sterilized BHI medium), topical wild type SE (1.0×$10^8$ CFU/cm$^2$ in 50% glycerol), and three doses of filaggrin-secreting SE constructs (SE$^{FLG}$) ($10^6$, $10^7$, and $10^8$ CFU/cm$^2$ in 50% glycerol). Each solution will be applied to the same ear and tail on each mouse daily for seven days, and mice be assessed on days 7, 14, 30, and 60 for microbiome analyses to assess colonization dynamics and on days 7 and 14 for microscopy and histology to assess localization and macroscopic changes in the skin (e.g., any signs of adverse events such as inflammation), etc. 12 mice in each arm per mouse type will be used. An overview of the study design is shown in FIG. 10.

Example 11. Colonization Dynamics and Persistence after Application of Filaggrin-Secreting SE In order to understand the influence of addition of SE on microbial load, microbial diversity, and stability of the skin microbiome, 16S rRNA sequencing will be used to measure the changes in the microbial community. Skin microbiome samples will be collected using flocked swabs from mouse tail skin at baseline, (day 0), days 7, 14, 30, and 60. DNA will be extracted using skin-specific custom protocols developed by the Oh Laboratory at The Jackson Laboratory for Genomic Medicine. To measure microbial load, qPCR using 16S rRNA V1-V3 primers will be used, as previously described. To examine microbial community dynamics, the V1-V3 will be amplified and sequenced using 2×300 bp read chemistry on an Illumina MiSeq platform. Sequences will be analyzed to the genus level as previously described[40], and operational taxonomic units (OTUs) will be defined at 97% similarity. Custom computational tools to differentiate staphylococcal species will be used to track relative abundance of applied SE [Oh et al., Genome Research 2013][67] (FIG. 6).

Dysbiosis will be measured using ecological metrics and community structure analyses. First, dysbiosis will be assessed as a function of diversity using the Shannon Diversity Index, which is an ecological measure of microbial communities that considers and will be compared before and after application. Additionally, community structures of the local microbiome before and after treatment will be compared. Dysbiosis will be measured as % overall deviation from (1) the baseline microbiome, and (2) deviation from the mean community structure across our controls. Statistics such as the Yue-Clayton index that compares community structures will be used. Finally, microbiome trends will be analyzed on a per-species level.

Because it is not anticipated that the S. epidermidis will result in elimination of the endogenous flora, the longitudinal dynamics of each species over the treatments will be tracked, to identify if species are being lost from the community at a targeted sequencing depth of 50,000 reads/sample.

Figure 11:
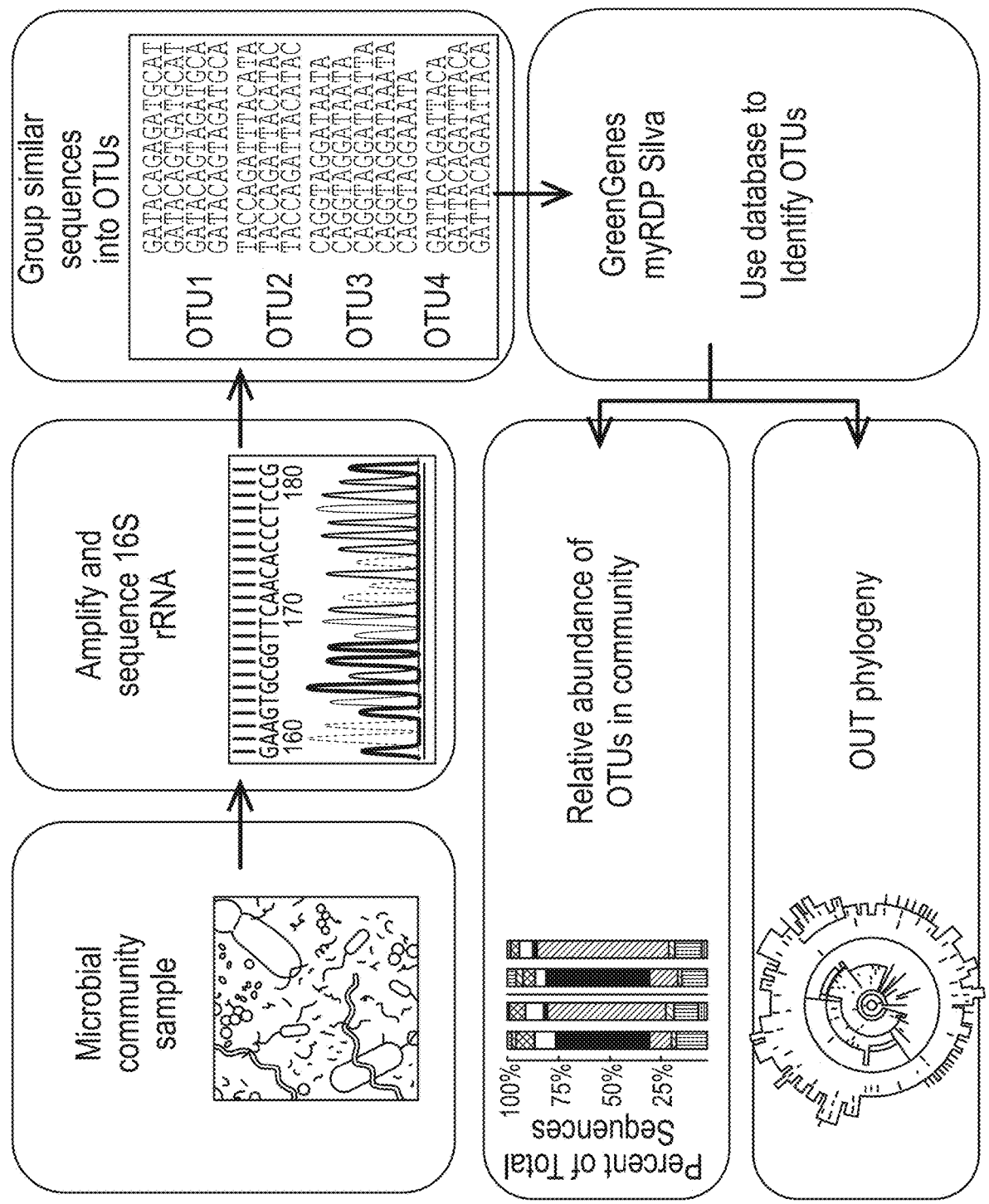
FIG. 11 shows experimental outline of 16S sequencing.

An experimental outline of the 16S sequencing is shown in FIG. 11.

Histology and Safety Analyses

Histology will be used to examine SE localization as well as an evaluation to probe safety and monitor any signs of inflammation. Excised ears of each group will be fixed in 4% paraformaldehyde for 16 h and will be embedded in paraffin. Then, 6 sm sections will be stained with hematoxylin (Sigma Aldrich, St Louis, MO, USA) and eosin (Sigma Aldrich, St Louis, MO, USA) (H&E). Infiltrated lymphocytes and spongiosis in the dermis will be observed by microscope (100×, 200×).

Statistical Analyses

Differences between groups for the primary outcome, the macroscopic clinical disease score, will be assessed using two-sided student t-tests, if the data are normally distributed. If not (for example, microbiome data), nonparametric equivalents such as the Wilcoxon-rank sum test will be used. Differences across groups will be assessed with ANOVA or nonparametric equivalents (Kruskal-Wallis). The same technique will be used for assessing the TEWL and the thickening of the epidermis. Finally, differences in ordinal variables will be assessed using Chi-square tests. All P-values will be corrected, if necessary, for multiple comparisons using false discovery rate. For analyses of the microbiome, community variation among samples will be calculated using the quantitative, taxonomy-based Yue-Clayton distance. Beta diversity metrics (e.g., Yue-Clayton theta (ϑ) index), a metric that measures the similarity between two samples, accounting for shared species and their abundance will be used. Pairwise comparisons between each sample within a timeseries will create a baseline for intramouse, longitudinal variation. For each set of successive samples, the ϑ index will be calculated. The ratio between successive ϑ and baseline ϑ will then be used as a flux score to proxy instability over time. This allows stability to be scored based on sliding windows rather than an aggregate comparison of differences over time, which can be a confounder in longitudinal data. Dynamical systems models for time series data, such as generalized Lotka-Volterra non-linear differential equation[63,64] time-dependent generalized additive models[65] or non-parametric methods, such as Gaussian Process Dynamical Models[66] will be investigated. For individual species, models such as the Augmented Dickey-Fuller test[67] will be used to test species' homeostasis. This will determine which species contribute to variation over time, as it is possible that select microbes can account for the majority of temporal variation.

Statistical Analyses

Unless otherwise indicated, experiments will be performed in triplicates, and means and standard deviations will be reported. For comparisons between groups, two-sided t-test or analysis of variance will be used. If data are not normally distributed, these will be replaced with non-parametric equivalents (Wilcoxon-rank sum and Kruskal-Wallis tests).

Safety and "Kill Switches"

A key requirement for nearly all recombinant microorganisms for clinical use is the ability to prevent undesired introduction to other individuals or environments. In order to ensure safety of the engineered strain, the present invention, in one embodiment, uses an auxotrophic strain, which requires supplementation of key amino acids (D-ala) or a certain metabolic gene (AlaR) for survival, and simultaneously replaces the need for an antibiotic resistant strain for selection, the latter of which is not commercially viable. In another embodiment, the present invention integrates a "kill switch", which is based on CRISPR/Cas9 self-cleavage upon induction of a dual xylose-riboswitch promoter. In yet another embodiment, the present invention provides cell counters, which recombine out the AZT locus after a defined number of divisions, although this method would necessitate reapplication of the vehicle. To ensure the safety of the engineered *S. epidermidis* of the present invention, a CRISPR/Cas9-based kill switch, which is xylose-inducible and doubly regulated with a theophylline riboswitch, is used. The basis of this approach is that Cas9 is extremely efficient at chromosomal cleavage given a targeting guide, and since staphylococci lack canonical non-homologous end joining repair pathways, genomic cleavage results in death in the absence of a homologous recombination template. The use of a CRISPR-based system also confers great specificity, since comparative genomics can be used to design guides unique to the engineered *S. epidermidis* strain of the present invention, such that the construct is inactive if spread to other microbes by horizontal gene transfer. Finally, in one embodiment, the present invention provides a construct designed to express multiple CRISPR spacers to simultaneously target multiple genomic regions to ensure cleavage and minimize survival by reversion.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

1. Wells R S, Kerr C B. Clinical features of autosomal dominant and sex-linked ichthyosis in an English population. British medical journal. 1966; 1(5493):947-950.
2. Hernandez-Martin A, Gonzalez-Sarmiento R, De Unamuno P. X-linked ichthyosis: an update. The British journal of dermatology. 1999; 141(4):617-627.
3. Marukian N V, Choate K A. Recent advances in understanding ichthyosis pathogenesis. F1000Research. 2016; 5:F1000 Faculty Rev-1497.
4. Oji V, Traupe H. Ichthyosis: clinical manifestations and practical treatment options. American journal of clinical dermatology. 2009; 10(6):351-364.
5. Sybert V P, Dale B A, Holbrook K A. Ichthyosis vulgaris: identification of a defect in synthesis of filaggrin correlated with an absence of keratohyaline granules. The Journal of investigative dermatology. 1985; 84(3):191-194.
6. Nirunsuksiri W, Presland R B, Brumbaugh S G, Dale B A, Fleckman P. Decreased Profilaggrin Expression in Ichthyosis Vulgaris Is a Result of Selectively Impaired Post-transcriptional Control. Journal of Biological Chemistry. 1995; 270(2):871-876.
7. Feinstein A, Ackerman A B, Ziprkowski L. Histology of autosomal dominant ichthyosis vulgaris and X-linked ichthyosis. Archives of dermatology. 1970; 101(5):524-527.
8. Osawa R, Akiyama M, Shimizu H. Filaggrin gene defects and the risk of developing allergic disorders. Allergology international: official journal of the Japanese Society of Allergology. 2011; 60(1):1-9.
9. Smith F J, Irvine A D, Terron-Kwiatkowski A, et al. Loss-of-function mutations in the gene encoding filaggrin cause ichthyosis vulgaris. Nature genetics. 2006; 38(3): 337-342.
10. Manabe M, Sanchez M, Sun T T, Dale B A. Interaction of filaggrin with keratin filaments during advanced stages of normal human epidermal differentiation and in ichthyosis vulgaris. Differentiation; research in biological diversity. 1991; 48(1):43-50.
11. Palmer C N, Irvine A D, Terron-Kwiatkowski A, et al. Common loss-of-function variants of the epidermal barrier protein filaggrin are a major predisposing factor for atopic dermatitis. Nature genetics. 2006; 38(4):441-446.
12. Weidinger S, Illig T, Baurecht H, et al. Loss-of-function variations within the filaggrin gene predispose for atopic dermatitis with allergic sensitizations. The Journal of allergy and clinical immunology. 2006; 118(1):214-219.
13. Marenholz I, Nickel R, Ruschendorf F, et al. Filaggrin loss-of-function mutations predispose to phenotypes involved in the atopic march. The Journal of allergy and clinical immunology. 2006; 118(4):866-871.
14. Sandilands A, Terron-Kwiatkowski A, Hull P R, et al. Comprehensive analysis of the gene encoding filaggrin uncovers prevalent and rare mutations in ichthyosis vulgaris and atopic eczema. Nature genetics. 2007; 39(5): 650-654.
15. Gruber R, Elias P M, Crumrine D, et al. Filaggrin genotype in ichthyosis vulgaris predicts abnormalities in epidermal structure and function. The American journal of pathology. 2011; 178(5):2252-2263.
16. Man M Q, Hatano Y, Lee S H, et al. Characterization of a hapten-induced, murine model with multiple features of atopic dermatitis: structural, immunologic, and biochemical changes following single versus multiple oxazolone challenges. The Journal of investigative dermatology. 2008; 128(1):79-86.
17. Fallon P G, Sasaki T, Sandilands A, et al. A homozygous frameshift mutation in the mouse Flg gene facilitates enhanced percutaneous allergen priming. Nature genetics. 2009; 41(5):602-608.
18. Oyoshi M K, Murphy G F, Geha R S. Filaggrin-deficient mice exhibit TH17-dominated skin inflammation and permissiveness to epicutaneous sensitization with protein antigen. The Journal of allergy and clinical immunology. 2009; 124(3):485-493, 493.e481.
19. Kawasaki H, Nagao K, Kubo A, et al. Altered stratum corneum barrier and enhanced percutaneous immune responses in filaggrin-null mice. The Journal of allergy and clinical immunology. 2012; 129(6):1538-1546.e1536.
20. Brown S J, McLean W H. One remarkable molecule: filaggrin. The Journal of investigative dermatology. 2012; 132(3 Pt 2):751-762.
21. Candi E, Schmidt R, Melino G. The cornified envelope: a model of cell death in the skin. Nature reviews Molecular cell biology. 2005; 6(4):328-340.
22. Miajlovic H, Fallon P G, Irvine A D, Foster T J. Effect of filaggrin breakdown products on growth of and protein expression by *Staphylococcus aureus*. The Journal of allergy and clinical immunology. 2010; 126(6):1184-1190.e1 183.
23. Vavrova K, Henkes D, Struver K, et al. Filaggrin deficiency leads to impaired lipid profile and altered acidification pathways in a 3D skin construct. The Journal of investigative dermatology. 2014; 134(3):746-753.
24. Jungersted J M, Scheer H, Mempel M, et al. Stratum corneum lipids, skin barrier function and filaggrin mutations in patients with atopic eczema. Allergy. 2010; 65(7): 911-918.
25. Sakai T, Hatano Y, Zhang W, Fujiwara S. Defective maintenance of pH of stratum corneum is correlated with preferential emergence and exacerbation of atopic-dermatitis-like dermatitis in flaky-tail mice. Journal of dermatological science. 2014; 74(3):222-228.
26. Bandier J, Johansen J D, Petersen L J, Carlsen B C. Skin pH, atopic dermatitis, and filaggrin mutations. Dermatitis: contact, atopic, occupational, drug. 2014; 25(3):127-129.
27. Ganemo A, Sjoden P O, Johansson E, Vahlquist A, Lindberg M. Health-related quality of life among patients with ichthyosis. European journal of dermatology: EJD. 2004; 14(1):61-66.
28. Ganemo A. Quality of life in Swedish children with congenital ichthyosis. Dermatology reports. 2010; 2(1): e7.
29. Dreyfus I, Pauwels C, Bourrat E, et al. Burden of inherited ichthyosis: a French national survey. Acta dermato-venereologica. 2015; 95(3):326-328.
30. Belkaid Y, Segre J A. Dialogue between skin microbiota and immunity. Science. 2014; 346(6212):954-959.
31. Belkaid Y, Tamoutounour S. The influence of skin microorganisms on cutaneous immunity. Nature reviews Immunology. 2016; 16(6):353-366.
32. Structure, function and diversity of the healthy human microbiome. Nature. 2012; 486(7402):207-214.
33. Wikoff W R, Anfora A T, Liu J, et al. Metabolomics analysis reveals large effects of gut microflora on mammalian blood metabolites. Proceedings of the National Academy of Sciences of the United States of America. 2009; 106(10):3698-3703.
34. Salzman N H, Hung K, Haribhai D, et al. Enteric defensins are essential regulators of intestinal microbial ecology. Nat Immunol. 2010; 11(1):76-82.
35. Kau A L, Ahern P P, Griffin N W, Goodman A L, Gordon J I. Human nutrition, the gut microbiome and the immune system. Nature. 2011; 474(7351):327-336.
36. Ravel J, Gajer P, Abdo Z, et al. Vaginal microbiome of reproductive-age women. Proceedings of the National Academy of Sciences of the United States of America. 2011; 108 Suppl 1:4680-4687.
37. Grice E A, Segre J A. The skin microbiome. Nature reviews Microbiology. 2011; 9(4):244-253.
38. Diaz Heijtz R, Wang S, Anuar F, et al. Normal gut microbiota modulates brain development and behavior. Proceedings of the National Academy of Sciences of the United States of America. 2011; 108(7):3047-3052.
39. Weyrich L S, Dixit S, Farrer A G, Cooper A J, Cooper A J. The skin microbiome: Associations between altered microbial communities and disease. The Australasian journal of dermatology. 2015.
40. Oh J, Byrd A L, Deming C, Conlan S, Kong H H, Segre J A. Biogeography and individuality shape function in the human skin metagenome. Nature. 2014; 514(7520):59-64.
41. Oh J, Freeman A F, Park M, et al. The altered landscape of the human skin microbiome in patients with primary immunodeficiencies. Genome research. 2013; 23(12): 2103-2114.
42. Grice E A. The skin microbiome: potential for novel diagnostic and therapeutic approaches to cutaneous disease. Seminars in cutaneous medicine and surgery. 2014; 33(2):98-103.
43. Powers C E, McShane D B, Gilligan P H, Burkhart C N, Morrell D S. Microbiome and pediatric atopic dermatitis. The Journal of dermatology. 2015.
44. Cogen A L, Yamasaki K, Sanchez K M, et al. Selective antimicrobial action is provided by phenol-soluble modulins derived from *Staphylococcus epidermidis*, a normal resident of the skin. J Invest Dermatol. 2010; 130(1):192-200.
45. Cogen A L, Yamasaki K, Muto J, et al. *Staphylococcus epidermidis* antimicrobial delta-toxin (phenol-soluble modulin-gamma) cooperates with host antimicrobial peptides to kill group A *Streptococcus*. PloS one. 2010; 5(1):e8557.
46. Monk I R, Shah I M, Xu M, Tan M W, Foster T J. Transforming the untransformable: application of direct transformation to manipulate genetically *Staphylococcus aureus* and *Staphylococcus epidermidis*. mBio. 2012; 3(2).
47. Wei W, Cao Z, Zhu Y L, et al. Conserved genes in a path from commensalism to pathogenicity: comparative phylogenetic profiles of *Staphylococcus epidermidis* RP62A and ATCC12228. BMC genomics. 2006; 7:112.

48. Bose J L, Fey P D, Bayles K W. Genetic tools to enhance the study of gene function and regulation in *Staphylococcus aureus*. Applied and environmental microbiology. 2013; 79(7):2218-2224.
49. Siprashvili Z, Nguyen N T, Bezchinsky M Y, Marinkovich M P, Lane A T, Khavari P A. Long-term type VII collagen restoration to human epidermolysis bullosa skin tissue. Hum Gene Ther. 2010; 21(10):1299-1310.
50. Johnson L N, Cashman S M, Read S P, Kumar-Singh R. Cell penetrating peptide POD mediates delivery of recombinant proteins to retina, cornea and skin. Vision Res. 2010; 50(7):686-697.
51. Hou Y W, Chan M H, Hsu H R, et al. Transdermal delivery of proteins mediated by non-covalently associated arginine-rich intracellular delivery peptides. Exp Dermatol. 2007; 16(12):999-1006.
52. Aufenvenne K, Larcher F, Hausser I, et al. Topical enzyme-replacement therapy restores transglutaminase 1 activity and corrects architecture of transglutaminase-1-deficient skin grafts. Am J Hum Genet. 2013; 93(4):620-630.
53. Park J, Ryu J, Jin L H, et al. 9-polylysine protein transduction domain: enhanced penetration efficiency of superoxide dismutase into mammalian cells and skin. Mol Cells. 2002; 13(2):202-208.
54. Lim J M, Chang M Y, Park S G, et al. Penetration enhancement in mouse skin and lipolysis in adipocytes by TAT-GKH, a new cosmetic ingredient. J Cosmet Sci. 2003; 54(5):483-491.
55. Schutze-Redelmeier M P, Kong S, Bally M B, Dutz J P. Antennapedia transduction sequence promotes anti tumour immunity to epicutaneously administered CTL epitopes. Vaccine. 2004; 22(15-16):1985-1991.
56. Lopes L B, Brophy C M, Furnish E, et al. Comparative study of the skin penetration of protein transduction domains and a conjugated peptide. Pharm Res. 2005; 22(5):750-757.
57. Nodake Y, Matsumoto S, Miura R, et al. Pilot study on novel skin care method by augmentation with *Staphylococcus epidermidis*, an autologous skin microbe—A blinded randomized clinical trial. Journal of dermatological science. 2015; 79(2):119-126.
58. Naik S, Bouladoux N, Linehan J L, et al. Commensal-dendritic-cell interaction specifies a unique protective skin immune signature. Nature. 2015; 520(7545):104-108.
59. Li D, Lei H, Li Z, Li H, Wang Y, Lai Y. A novel lipopeptide from skin commensal activates TLR2/CD36-p38 MAPK signaling to increase antibacterial defense against bacterial infection. PloS one. 2013; 8(3):e58288.
60. Lai Y, Cogen A L, Radek K A, et al. Activation of TLR2 by a small molecule produced by *Staphylococcus epidermidis* increases antimicrobial defense against bacterial skin infections. J Invest Dermatol. 2010; 130(9):2211-2221.
61. Naik S, Bouladoux N, Wilhelm C, et al. Compartmentalized control of skin immunity by resident commensals. Science. 2012; 337(6098):1115-1119.
62. Gonzalez F J, Valdes-Rodriguez R, Ramirez-Elias M G, Castillo-Martinez C, Saavedra-Alanis V M, Moncada B. Noninvasive detection of filaggrin gene mutations using Raman spectroscopy. Biomedical optics express. 2011; 2(12):3363-3366.
63. Harding C R, Aho S, Bosko C A. Filaggrin-revisited. International Journal of Cosmetic Science. 2013; 35(5): 412-423.
64. Sandilands A, Sutherland C, Irvine A D, McLean W H. Filaggrin in the frontline: role in skin barrier function and disease. Journal of cell science. 2009; 122(Pt 9):1285-1294.
65. Denecker G, Hoste E, Gilbert B, et al. Caspase-14 protects against epidermal UVB photodamage and water loss. Nature cell biology. 2007; 9(6):666-674.
66. Kamata Y, Taniguchi A, Yamamoto M, et al. Neutral cysteine protease bleomycin hydrolase is essential for the breakdown of deiminated filaggrin into amino acids. The Journal of biological chemistry. 2009; 284(19):12829-12836.
67. Oh J, Freeman A F, Program NCS, et al. The altered landscape of the human skin microbiome in patients with primary immunodeficiencies. Genome research. 2013; 23(12):2103-2114.

What is claimed is:

1. A recombinant microorganism capable of secreting a filaggrin polypeptide, wherein the recombinant microorganism is *Staphylococcus epidermidis*, comprising an expression vector comprising a first coding sequence comprising a gene capable of expressing the filaggrin polypeptide and a second coding sequence comprising a gene capable of expressing a cell penetrating peptide, wherein the filaggrin polypeptide comprises an amino acid sequence at least 98% identical to SEQ ID NO: 1.

2. The recombinant microorganism of claim 1, further comprising a third coding sequence comprising a gene capable of expressing an export signal.

3. The recombinant microorganism of claim 1, wherein the microorganism secretes a filaggrin fusion protein.

4. A live biotherapeutic composition comprising a recombinant microorganism capable of secreting a filaggrin polypeptide, wherein the recombinant microorganism is *Staphylococcus epidermidis*, comprising
   (i) a first coding sequence comprising a nucleic acid sequence capable of expressing the filaggrin therapeutic polypeptide, wherein the filaggrin polypeptide comprises an amino acid sequence at least 98% identical to SEQ ID NO: 1;
   (ii) a second coding sequence comprising a nucleic acid sequence capable of expressing a cell penetrating peptide;
   (iii) a third coding sequence comprising a nucleic acid sequence capable of expressing an export signal; and
   (iv) a promoter operably linked to the first coding sequence, the second coding sequence and the third coding sequence;

wherein the first coding sequence, second coding sequence and first coding sequence is capable of expressing a filaggrin fusion product, or variant thereof.

5. The composition of claim 4, comprising a pharmaceutically acceptable carrier, wherein the pharmaceutically acceptable carrier is selected from the group consisting of an aqueous solution, an emulsion, a cream, a lotion, a gel, or an ointment.

6. A method for producing a live biotherapeutic composition, the method comprising:
   (a) transfecting a *Staphylococcus epidermidis* cell with an expression vector comprising a first coding sequence comprising a gene capable of expressing the filaggrin polypeptide and a second coding sequence comprising a gene capable of expressing a cell penetrating peptide, wherein the filaggrin polypeptide comprises an amino acid sequence at last 98% identical to SEQ ID NO: 1; and
   (b) allowing the transfected cell to produce a therapeutic polypeptide fusion protein; and
   (c) obtaining the live biotherapeutic composition.

7. The method of claim 6, further comprising (iii) transfecting the cell with a third coding sequence comprising a nucleic acid sequence capable of expressing an export signal.

8. A method of treating a skin disease comprising administering to a subject in need thereof the composition of claim 1.

9. The method of claim 8, wherein the skin disease is Ichthyosis vulgaris (IV).

10. The method of claim 8, wherein the skin disease is atopic dermatitis.

* * * * *